(12) United States Patent
Dutta

(10) Patent No.: US 10,125,127 B2
(45) Date of Patent: Nov. 13, 2018

(54) NEUROPROTECTIVE AGENTS FOR TREATMENT OF NEURODEGENERATIVE DISEASES

(71) Applicant: WAYNE STATE UNIVERSITY, Detroit, MI (US)

(72) Inventor: Aloke K. Dutta, Troy, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/648,413

(22) PCT Filed: Nov. 27, 2013

(86) PCT No.: PCT/US2013/072253
§ 371 (c)(1),
(2) Date: May 29, 2015

(87) PCT Pub. No.: WO2014/085600
PCT Pub. Date: Jun. 5, 2014

(65) Prior Publication Data
US 2015/0299180 A1    Oct. 22, 2015

Related U.S. Application Data

(60) Provisional application No. 61/731,096, filed on Nov. 29, 2012.

(51) Int. Cl.
*C07D 277/82* (2006.01)
*C07D 417/12* (2006.01)
(Continued)

(52) U.S. Cl.
CPC .......... *C07D 417/12* (2013.01); *A61K 31/428* (2013.01); *A61K 31/496* (2013.01);
(Continued)

(58) Field of Classification Search
CPC .. C07D 417/12; C07D 277/82; C07D 417/14; A61K 31/517; A61K 31/428; A61K 31/496
See application file for complete search history.

(56) References Cited

U.S. PATENT DOCUMENTS 6,982,332 B2 *   1/2006   Dutta ................... A61K 31/495
                                                            544/253
2005/0032856 A1   2/2005   Bennett
(Continued)

FOREIGN PATENT DOCUMENTS

WO       WO 96/08228       *  3/1996
WO       WO 96/08228 A2   *  3/1996
(Continued)

OTHER PUBLICATIONS

Dutta, A.K.,"A novel series of hybrid compounds derived by combining 2-aminotetralin and piperazine fragments: Binding activity at D 2 and D 3 receptors." Bioorganic & medicinal chemistry letters 12.4 (2002): 619-622.*
Biswas, S., "Further structure-activity relationships study of hybrid 7-{[2-(4-phenylpiperazin-1-yl) ethyl] propylamino}-5, 6, 7, 8-tetrahydronaphthalen-2-ol analogues: identification of a high-affinity D3-preferring agonist with potent in vivo activity with long duration of action." Journal of medicinal chemistry 51.1 (2007): 101-117.*
Brown, D.A., "Investigation of various N-heterocyclic substituted piperazine versions of 5/7-{[2-(4-aryl-piperazin-1-yl)-ethyl]-propyl-amino}-5, 6, 7, 8-tetrahydro-naphthalen-2-ol: Effect on affinity and selectivity for dopamine D3 receptor." Bioorganic & medicinal chemistry 17.11 (2009): 3923-3933.*
(Continued)

*Primary Examiner* — John M Mauro
(74) *Attorney, Agent, or Firm* — Brooks Kushman P.C.

(57) ABSTRACT

A compound having formula I is useful for treating a neurodegenerative disease:

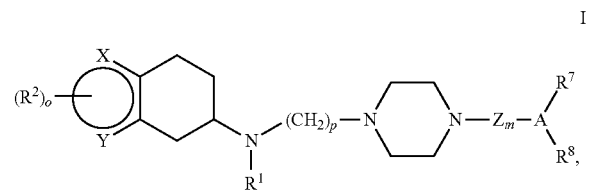

$R^1$ is an $C_{1-12}$ organyl group;

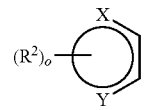

is a $C_{1-12}$ heterocyclic ring system containing 5 to 12 ring atoms and up to three heteroatoms individually selected from the group consisting of N, O, S, and Se;
$R^2$ are $C_{1-12}$ organyl groups;
$R^7$, $R^8$ are each independently, hydrogen (H), hydroxyl, oxo (i.e., carbonyl), $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or $-NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;
o is 0, 1, 2, 3, or 4;
A is a $C_{6-12}$ aryl group, $C_{5-12}$ heteroaryl group, or an optionally substituted 3-hydroxypyridin-4(1H)-one;
p is an integer from 1 to 6; and
$Z_m$ is absent or a divalent linking moiety; and
m is an integer representing the number of time Z is repeated.

16 Claims, 18 Drawing Sheets

(51) Int. Cl.
C07D 417/14 (2006.01)
A61K 31/496 (2006.01)
A61K 31/428 (2006.01)
A61K 31/517 (2006.01)

(52) U.S. Cl.
CPC .......... *A61K 31/517* (2013.01); *C07D 277/82* (2013.01); *C07D 417/14* (2013.01)

(56) References Cited

U.S. PATENT DOCUMENTS

2006/0020132 A1  1/2006  Dutta
2011/0046153 A1  2/2011  Stark et al.
2012/0108815 A1  5/2012  Wayne

FOREIGN PATENT DOCUMENTS

WO          02-098367 A2      12/2002
WO     WO 2010/123995    * 10/2010
WO     WO 2010123995 A1 * 10/2010  ............. A61K 31/50

OTHER PUBLICATIONS

Brown, D.A., "Structurally constrained hybrid derivatives containing octahydrobenzo [g or f] quinoline moieties for dopamine D2 and D3 receptors: binding characterization at D2/D3 receptors and elucidation of a pharmacophore model." Journal of medicinal chemistry 51.24 (2008): 7806.*

Chen, J., "High-affinity and selective dopamine D 3 receptor full agonists." Bioorganic & medicinal chemistry letters 22.17 (2012): 5612-5617.*

Dutta, A.K., "Synthesis and biological characterization of novel hybrid 7-{[2-(4-phenyl-piperazin-1-yl)-ethyl]propyl-amino}-5, 6, 7, 8-tetrahydro-naphthalen-2-ol and their heterocyclic bioisosteric analogues for dopamine D2 and D3 receptors." Bioorganic & medicinal chemistry 12.16 (2004): 4361-4373.*

Ghosh, B., "Further delineation of hydrophobic binding sites in dopamine D 2/D 3 receptors for N-4 substituents on the piperazine ring of the hybrid template 5/7-{[2-(4-aryl-piperazin-1-yl)-ethyl]-propyl-amino}-5, 6, 7, 8-tetrahydro-naphthalen-2-ol." Bioorganic & medicinal chemistry 18.15 (2010): 5661-5674.*

Ghosh, B., "Development of (S)-N6-(2-(4-(Isoquinolin-1-yl) piperazin-1-yl) ethyl)-N6-propyl-4, 5, 6, 7-tetrahydrobenzo [d]-thiazole-2, 6-diamine and its analogue as a D3 receptor preferring agonist: Potent in vivo activity in Parkinson's disease animal models." Journal of medicinal chemistry 53.3 (2010): 1023-1037.*

Kortagere, S., "Interaction of novel hybrid compounds with the D3 dopamine receptor: Site-directed mutagenesis and homology modeling studies." Biochemical pharmacology 81.1 (2011): 157-163.*

Ghosh, B., "Development of (S)-N 6-(2-(4-(Isoquinolin-1-yl) piperazin-1-yl) ethyl)N 6-propyl-4, 5, 6, 7-tetrahydrobenzo [d]-thiazole-2, 6-diamine and Its Analogue as a D3 Receptor Preferring Agonist: Potent in Vivo Activity in Parkinson's Disease Animal Models." *Journal of medicinal chemistry* 53.3 (2009): 1023-1037.*

Biswas, S. et al., "Bioisosteric Heterocyclic Versions of 7-{[2-(4-Phenyl-piperazin-1-yl)ethyl]propy Identification of Highly Potent and Selective Agonists for Dopamine D3 Receptor with Potent In Vivo Activity," J. Med. Che. 2008, 51, pp. 3005-3019.

Partial Supplementary European Search Report dated Jun. 13, 2016 for EP Appn. No. 13859526.9, 2 pgs.

Johnson, M. et al., "Structure-Activity Relationship Study of N6-(2(4-(1H-indol-5-yl)piperazin-1-yl)ethyl)-N6-propyl-4,5,6,7-tetrahydrobenzo[d]thiazole-2,6-diamine analogues: Development of highly selective D3 dopamine receptor agonists along with a highly potent D2/D3 agonist and their pharmacological characterization," J Med Chem. 2012, 55(12), pp. 5826-5840.

Wang, C.H. et al., "Novel synthesis and functionalization of orth-ortho disubstituted biphenyls and a highly condensed novel heterocycle using radical cylization reaction," Tetrahedron 68 (2012, pp. 9750-9762.

International Search Report dated Mar. 5, 2014 from PCT/US2013/072253, filed Nov. 27, 2013, 3 pgs.

Johnson, M. et al., Correction to Structure-Activity Relationship Study of N6-(2-(4-(1H-Indol-5-yl)piperazin-1-yl)ethyl)-N6-propyl-4,5,6,7-tetrahydrobenzol[d]thiazole-2,6-diamine Analogues: Development of Highly Selective D3 Dopamine Receptor Agonists along with a Highly Potent D2/D3 Agonist and Their Pharmacological Characterization, J. of J. Med. Chem., Jan. 4, 2013, 56, pp. 589-590.

Johnson, M. et al., Correction to Structure-Activity Relationship Study of N6-(2-(4-(1H-Indol-5-yl)piperazin-1-yl)ethyl)-N6-propyl-4,5,6,7-tetrahydrobenzol[d]thiazole-2,6-diamine Analogues: Development of Highly Selective D3 Dopamine Receptor Agonists along with a Highly Potent D2/D3 Agonist and Their Pharmacological Characterization, J. of J. Med. Chem. 2013, 56, pp. 589-590.

* cited by examiner

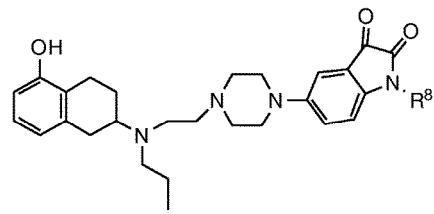
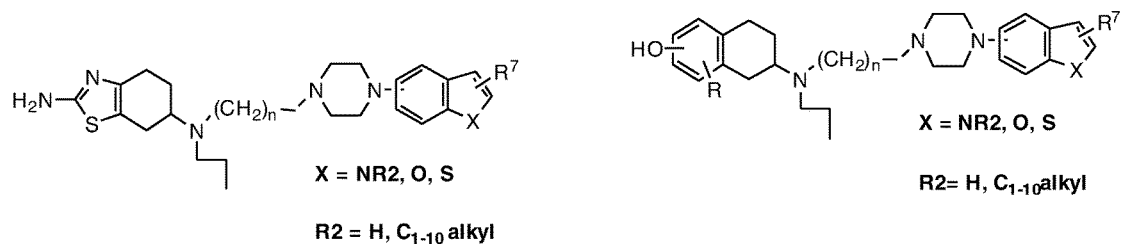
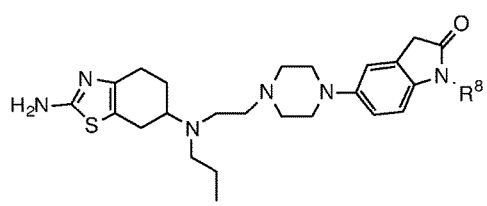
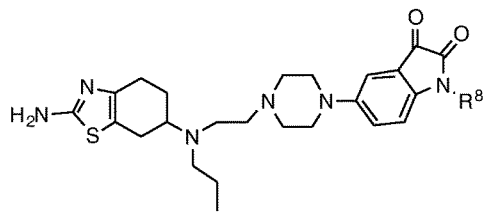
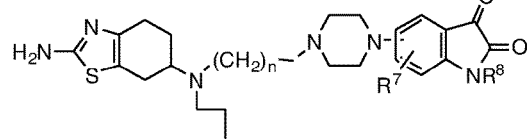
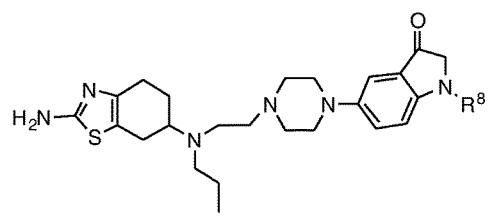
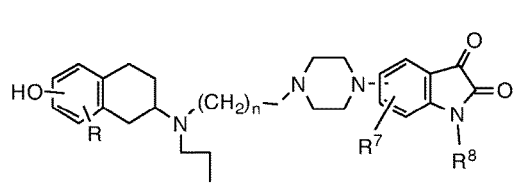
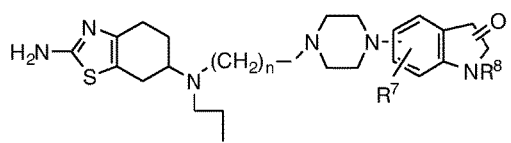
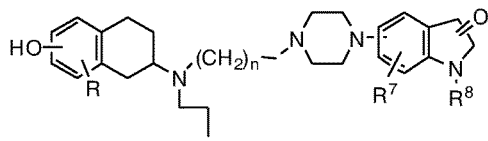
Fig. 4

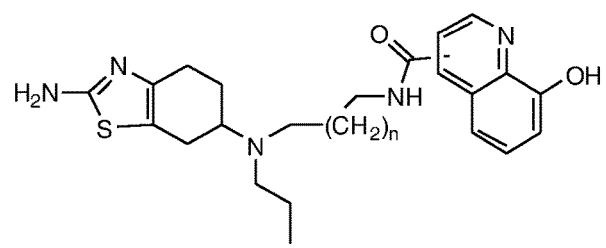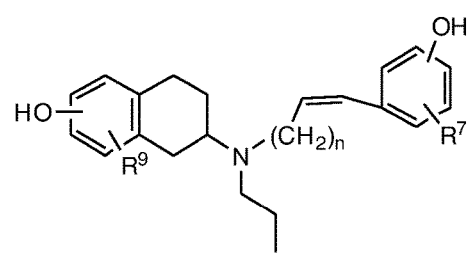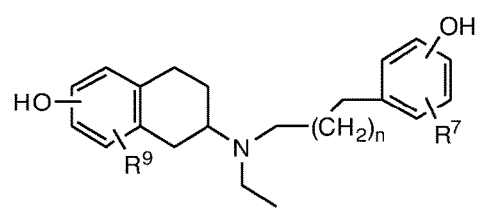
Fig. 8

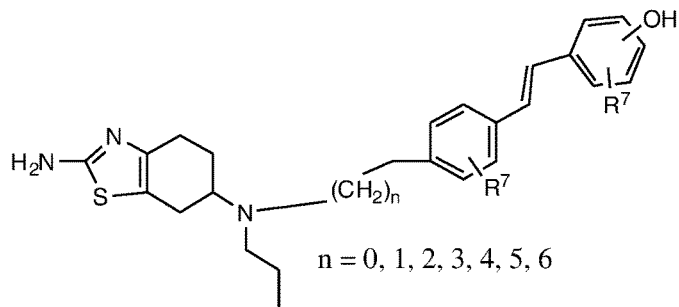
n = 0, 1, 2, 3, 4, 5, 6
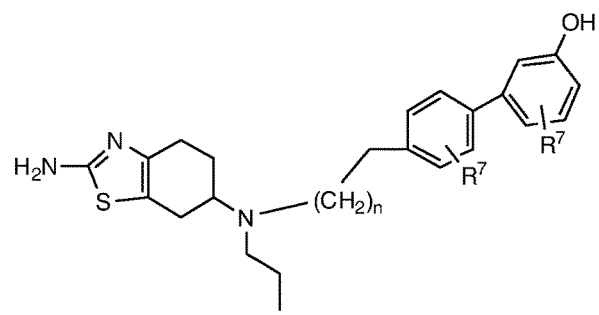
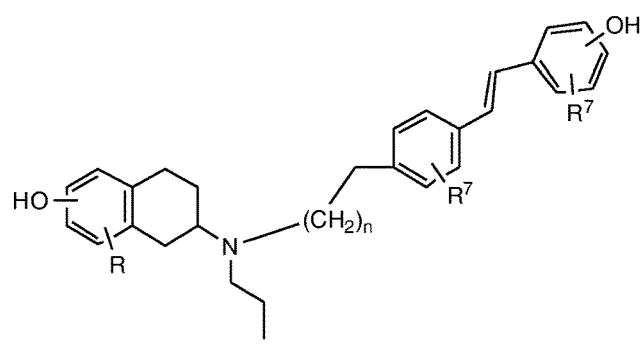
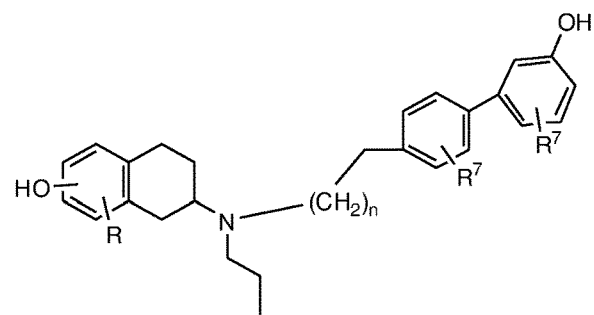
Fig. 9

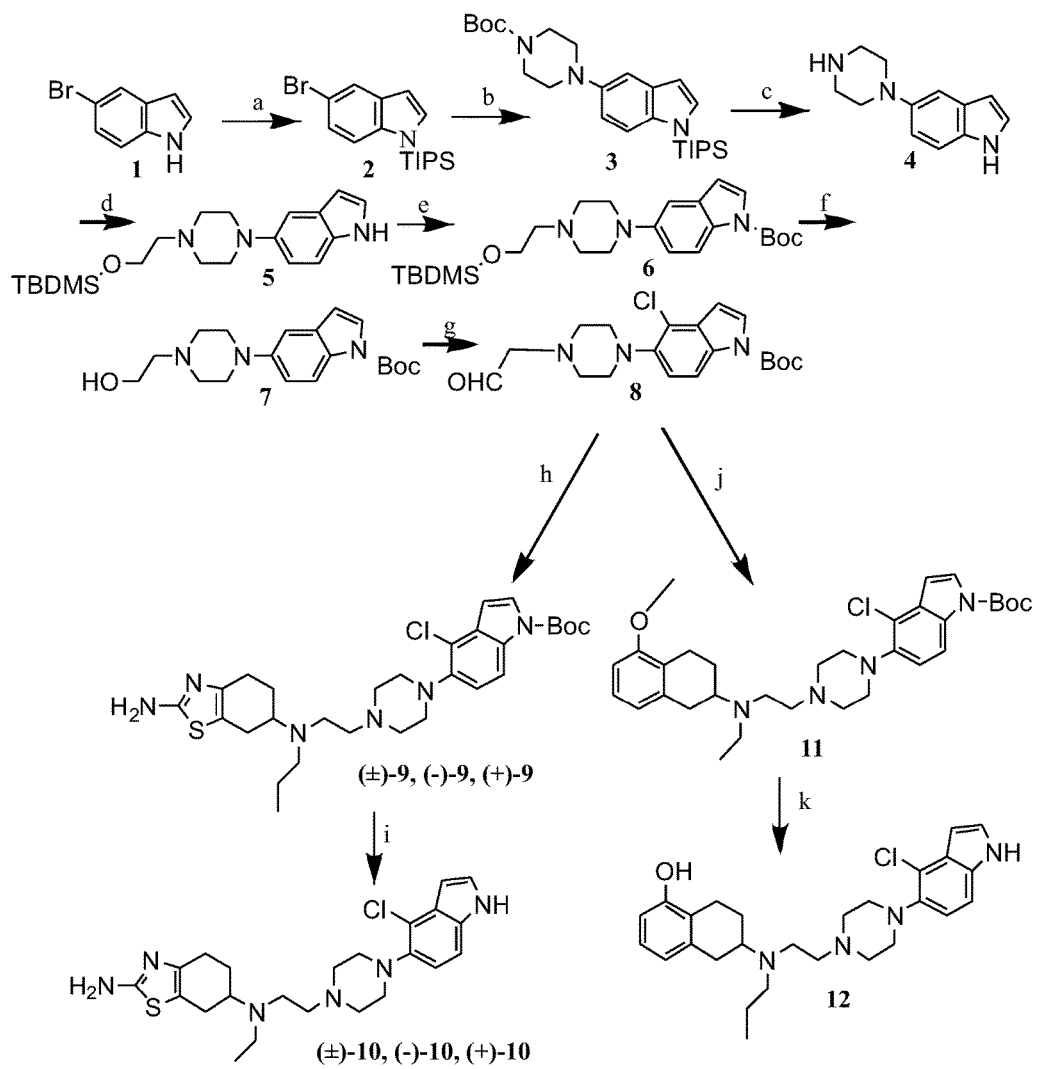

Scheme 2. Reagents and conditions: (a) triisopropylsilyl chloride, NaH, THF; (b) 4, PdCl$_2$[P(o-tol)$_3$]$_2$, NaOtBu, xylenes, reflux; (c) CF$_3$COOH, CH$_2$Cl$_2$; (d) (2-bromo-ethoxyl)-tert-butyl-dimethyl silane, K$_2$CO$_3$, CH$_3$CN, reflux; (e) (Boc)$_2$O, DMAP, THF; (f) n-Bu$_4$NF, THF; (g) (COCl)$_2$, DMSO Et$_3$N, CH$_2$Cl$_2$, -78 °C-rt; (h) (±), (-) or (+)-pramipexole, Na(OAc)$_3$BH, CH$_2$Cl$_2$; (i) CF$_3$COOH, CH$_2$Cl$_2$; (j) 2, Na(OAc)$_3$BH, CH$_2$Cl$_2$; (k) aq. HBr (48%), reflux.

Fig. 12

Reaction and Conditions: (a) TPP, toluene, reflux, 16 h, 87%; (b) 1 M NaOH aq., 15 min, 88%; (c) vanillin, CHCl$_3$, reflux, 5 h, 85%; (d) TBDMSCl, imidazole, DMF, rt, 2 h, 90%; (e) DIBALH, THF, -10 ;æ to rt, 6 h, 94%; (f) MnO$_2$, DCM, rt, 24 h, 84%; (g) TBAF, THF, 0 ;æ, 1 h, 84%; (h) (;Å) Pramipexole, NaBH(OAc)$_3$, DCM, rt, 48 h, 30%.

NEUROPROTECTIVE AGENTS FOR TREATMENT OF NEURODEGENERATIVE DISEASES

CROSS-REFERENCE TO RELATED APPLICATIONS

This application is the U.S. national phase of PCT Application No. PCT/US2013/072253 filed Nov. 27, 2013, which claims the benefit of U.S. Ser. No. 61/731,096 filed Nov. 29, 2012, the disclosures of which are incorporated in their entirety by reference herein.

STATEMENT REGARDING FEDERALLY SPONSORED RESEARCH OR DEVELOPMENT

The invention was made with Government support under Contract No. NS047198 awarded by the National Institutes of Health/National Institute of Neurological Disorders and Stroke. The Government has certain rights to the invention.

TECHNICAL FIELD

The present invention relates to compounds for treating neurodegenerative diseases.

BACKGROUND OF THE INVENTION

Dopaminergic receptor systems have been targeted for the development of pharmacotherapeutic agents for a number of CNS related disorders, including drug addiction, schizophrenia, depression, and Parkinson's disease (PD). Dopamine (DA) receptor agonists have been employed more extensively in the treatment of Parkinson's disease than any other type of pharmacotherapy. Levodopa (L-dopa), the immediate precursor to endogenous DA, is the current gold-standard treatment option for PD. DA receptors belong to the family of transmembrane proteins known as G-protein-coupled receptors (GPCRs). DA receptors are widely distributed in the CNS, are also present in the periphery, and are divided into five subtypes. On the basis of the stimulatory action on adenylyl cyclase, D1 and D5 are grouped together as D1 type. D2-D4 receptors are classified as D2 type because of their inhibitory action on adenylyl cyclase activity. Interestingly, the D3 receptor was found to have a distribution in the brain that is somewhat different from that of the D2 receptor. The highest levels of D3 receptor expression were found to be in the limbic region of the brain, while D2 receptor expression is most dense in the striatum of the midbrain. D2 and D3 receptor subtypes occur post- and presynaptically. In the latter location they function as autoreceptors that regulate DA synthesis, metabolism, and release. It is noteworthy that D2 and D3 receptor subtypes share 50% overall amino acid sequence homology and 75-80% in their agonist binding sites. As a result, development of ligands selective for either subtype is a challenging task.

Parkinson's disease (PD) is a progressive, neurodegenerative disorder that results from the death of DA-producing cells in the substantia nigra region of the midbrain. Common symptoms include resting tremor, muscular rigidity, bradykinesia, postural instability, and cognitive psychiatric complications. Although the etiology of PD is not yet clear and may be multifactorial, oxidative stress and mitochondrial dysfunction are thought to play a central role in the pathology of the disease. Recent studies on various genetic mutations have provided new insights into the disease process. Oxidative stress has been strongly implicated in midbrain dopaminergic cell death. Toxicity from endogenous and exogenous origins, caused by oxidative mechanisms, has been implicated as a fundamental process in progressive nigral cell loss. Along with motor fluctuations and wearing off after long-term treatment, side effects associated with L-dopa treatment and the eventual oxidation of DA derived from L-dopa have been speculated to produce further oxidative stress.

In addition, α-synuclein, a presynaptic protein involved in fibrillization, has been implicated in the pathogenesis of PD. A recent report demonstrated that in cultured human dopaminergic neurons, accumulation of α-synuclein induces apoptosis in the presence of DA and reactive oxygen species. Furthermore, an interaction between calcium, cytosolic DA, and α-synuclein has been implicated in the loss of DA neurons in the substantia nigra. In this case, DAdependent neurotoxicity is mediated by a soluble protein complex containing α-synuclein. Therefore, α-synuclein, together with oxidized DA, could have synergistic effects in terms of disease susceptibility and progression.

Accordingly, there is a need for dopamine improved D2/D3 agonist molecules, and in particular, for improved D2/D3 agonist molecules with a capacity to bind to iron.

SUMMARY OF THE INVENTION

In at least one embodiment, the present invention solves one or more problems of the prior art by providing a compound having formula I for treating a neurodegenerative disease:

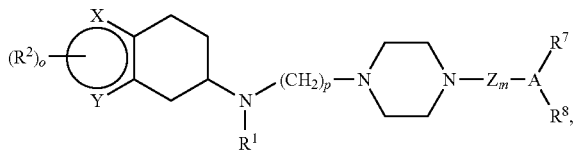

I $R^1$ is an $C_{1-12}$ organyl group;

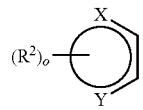

is an aromatic and optionally $C_{1-12}$ heterocyclic ring system containing 5 to 12 ring atoms and up to three heteroatoms individually selected from the group consisting of N, O, S, and Se;

$R^2$ are $C_{1-12}$ organyl groups;

$R^7$, $R^8$ are each independently, hydrogen (H), hydroxyl, oxo (i.e., carbonyl), $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or $-NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

o is 0, 1, 2, 3, or 4;

A is a $C_{6-12}$ aryl group, $C_{5-12}$ heteroaryl group, or an optionally substituted 3-hydroxypyridin-4(1H)-one;

p is an integer from 1 to 6; and $Z_m$ is absent or a divalent linking moiety; and m is an integer representing the number of time Z is repeated.

In another embodiment, a compound having formula II for treating neurodegenerative and other related CNS diseases is provided:

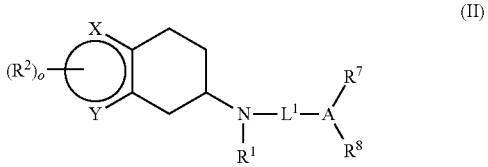

where $R^1$, $R^2$, o, p, X, Y, and A are the same as set forth above. $L^1$ is a linking group. In a refinement, $L^1$ is $(CH_2)_n$, $(CH_2)_n CO$, $(CH_2)_n NCO(CH_2)_k$, $C_{1-10}$ carboximido, $C_{1-10}$ alkanediyl, $C_{2-10}$ alkenediyl, $C_{2-10}$ alkynediyl, $-(CH2)_n-CO-CH=CH-$, or $-(CH_2)n-CH=CH-CO-$; where n and k are integers from 0 to 8; and $R^7$, $R^8$ each independently, hydrogen (H), hydroxyl, oxo (i.e., carbonyl), $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo (preferably fluoro or chloro), $C_{1-4}$ aldehyde, or $-NR^4_q$ and like groups where $R^4$ is H or organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl.

BRIEF DESCRIPTION OF THE DRAWINGS

Exemplary embodiments of the present invention will become more fully understood from the detailed description and the accompanying drawings, wherein:

FIGS. 1-6 provide compounds having formula I;

FIGS. 7-10 provide examples of compounds having formula II;

FIG. 12 provides a synthetic scheme for compounds having formula I;

DETAILED DESCRIPTION OF THE INVENTION

Figure 1:
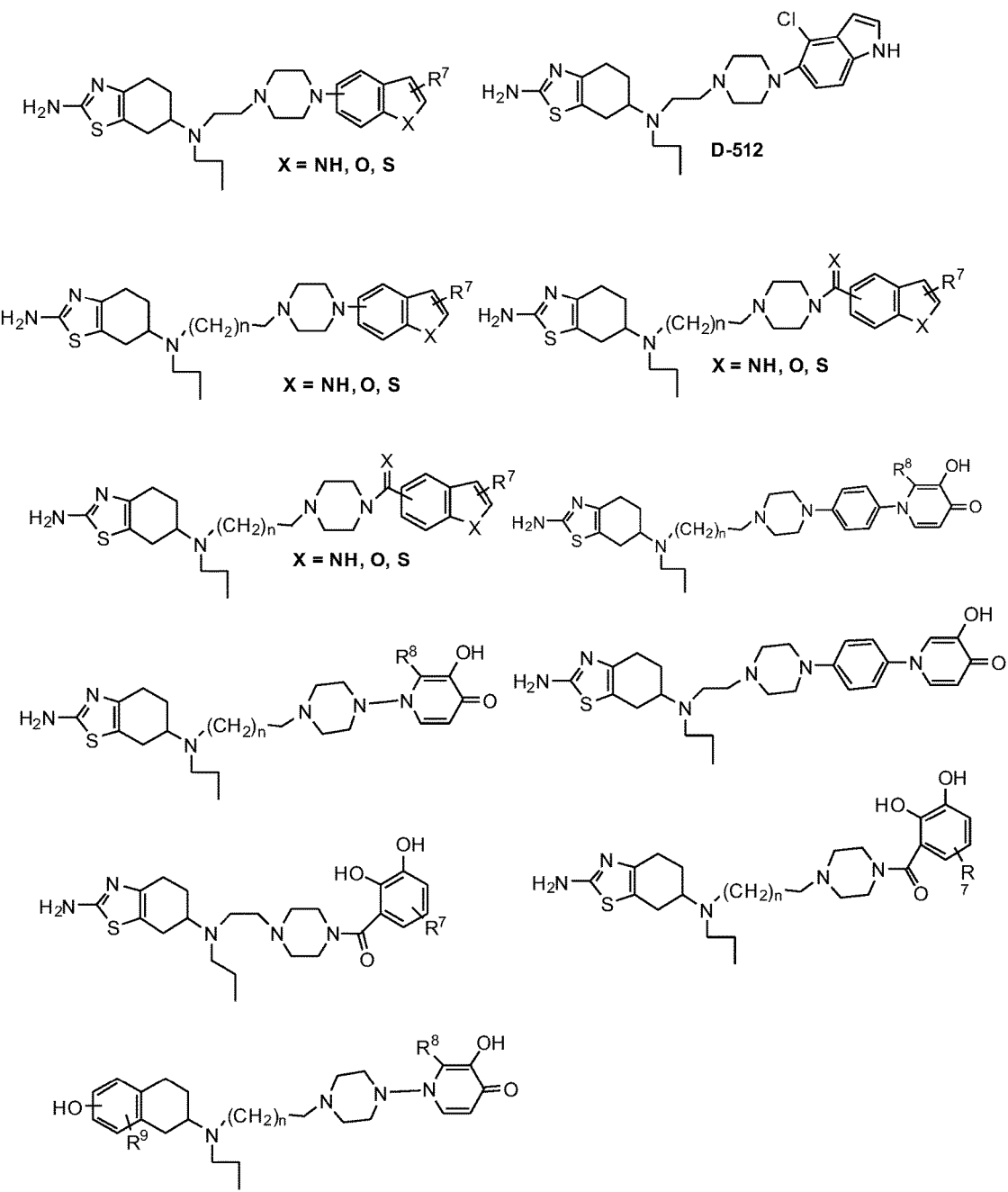
Figure 2:
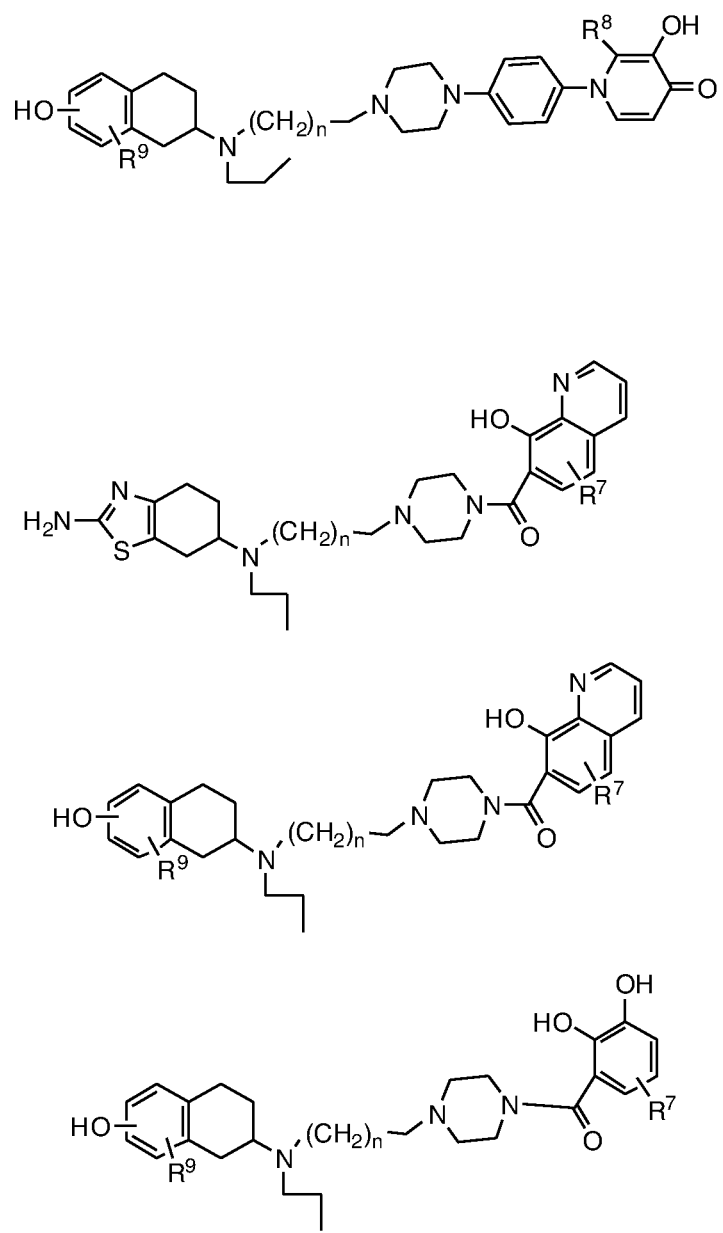
Figure 3:
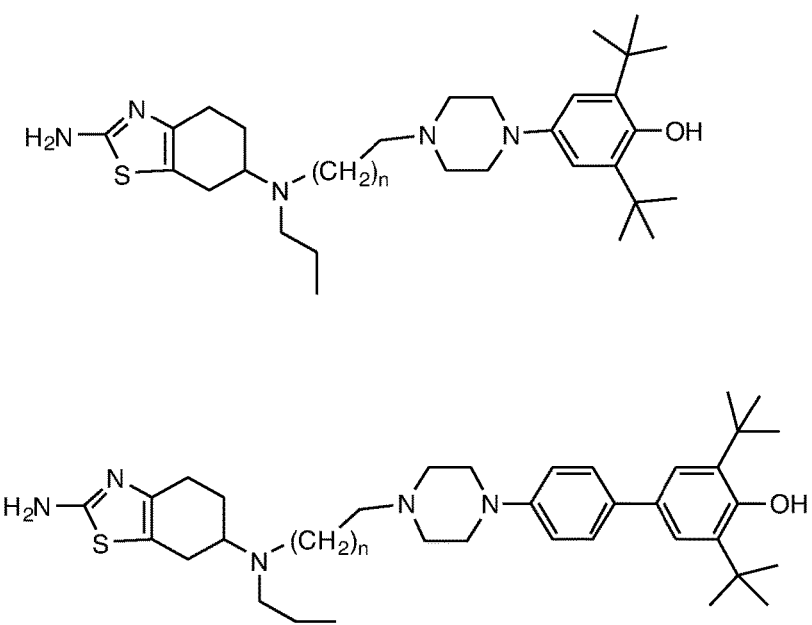
Figure 5:
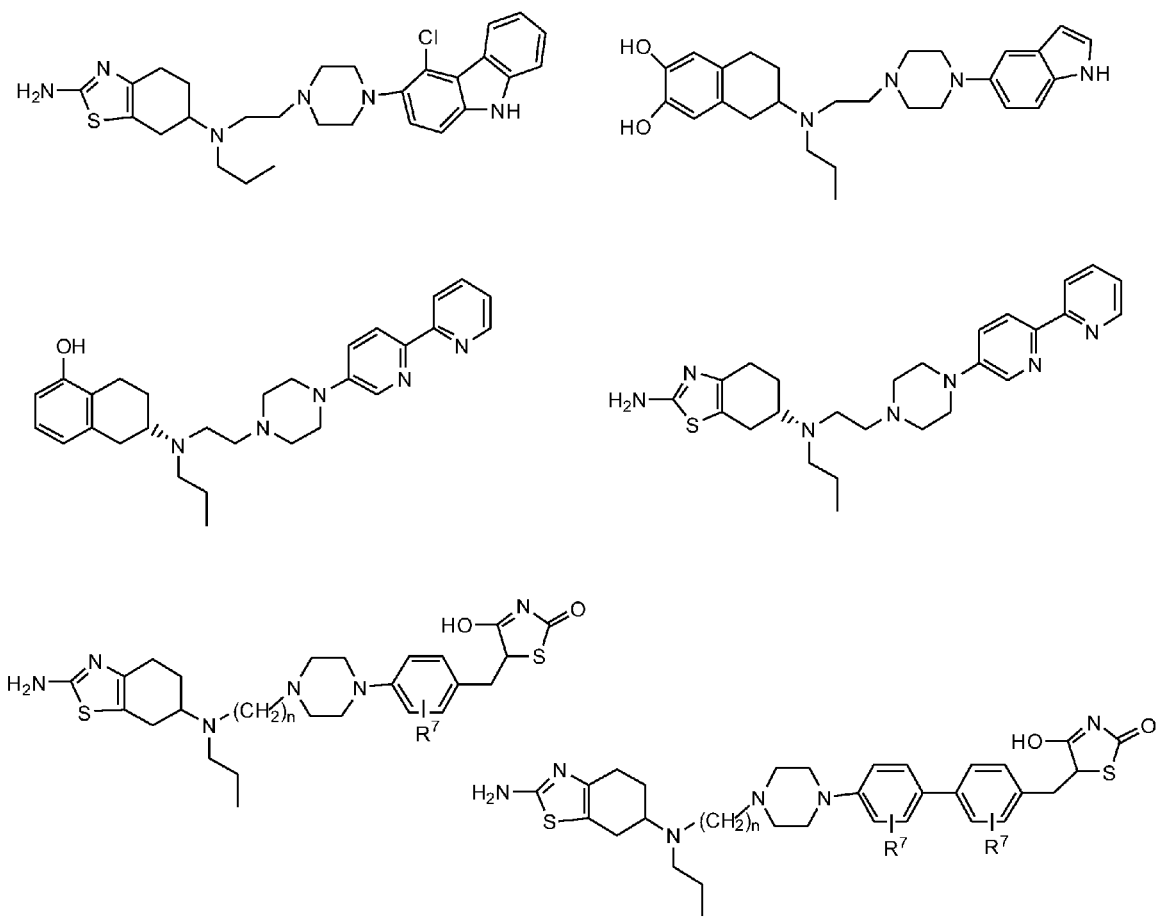
Figure 6:
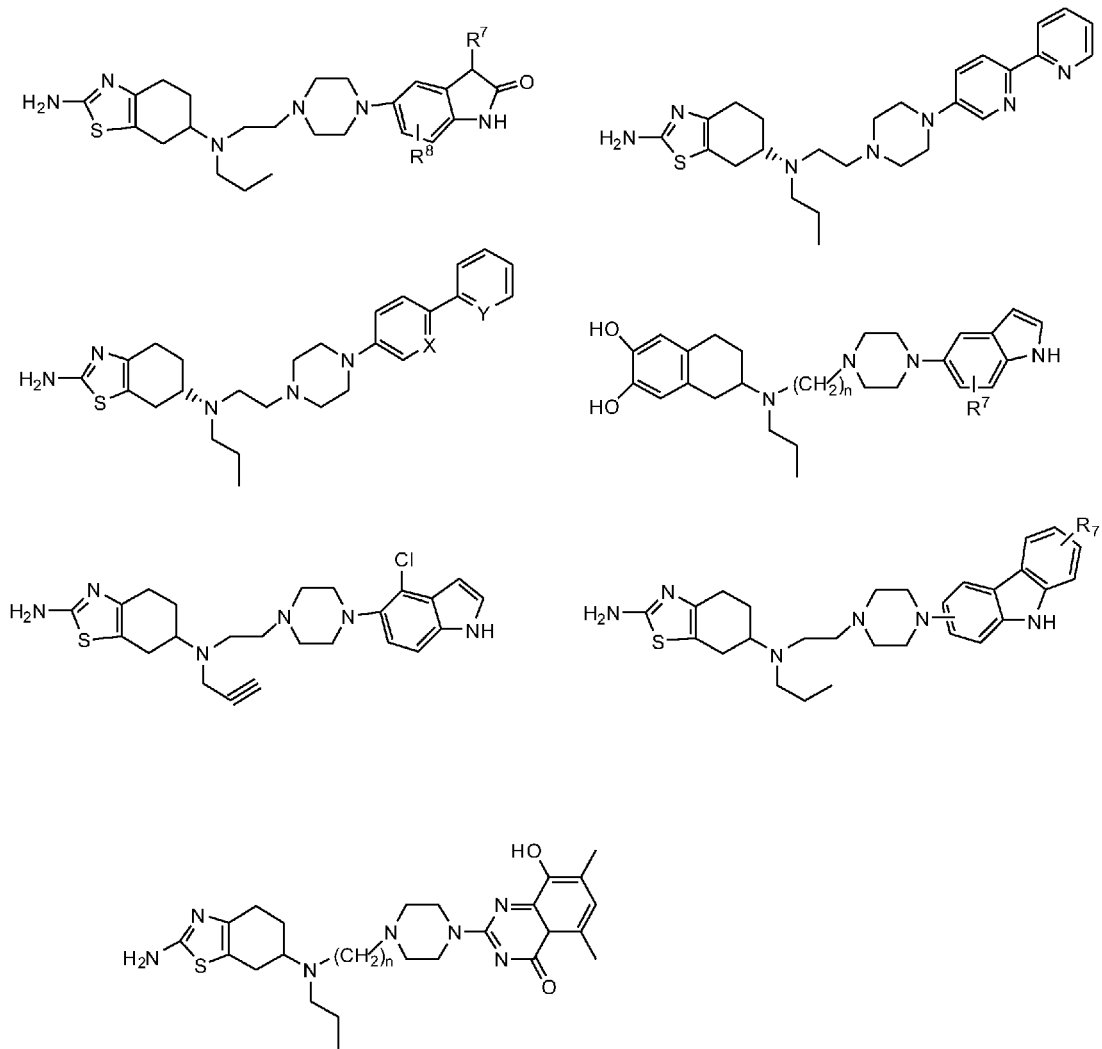
Figure 7:
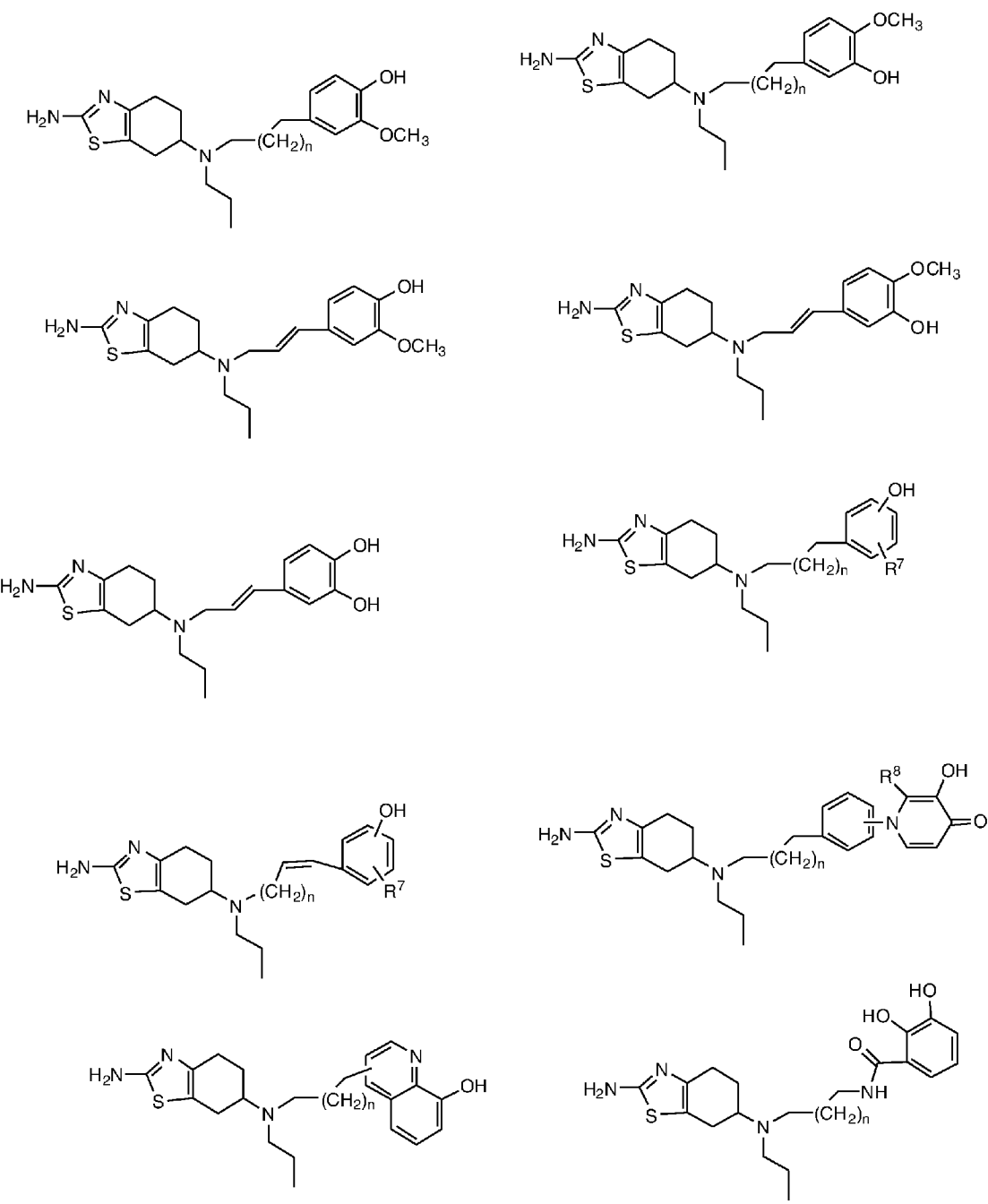
Figure 10:
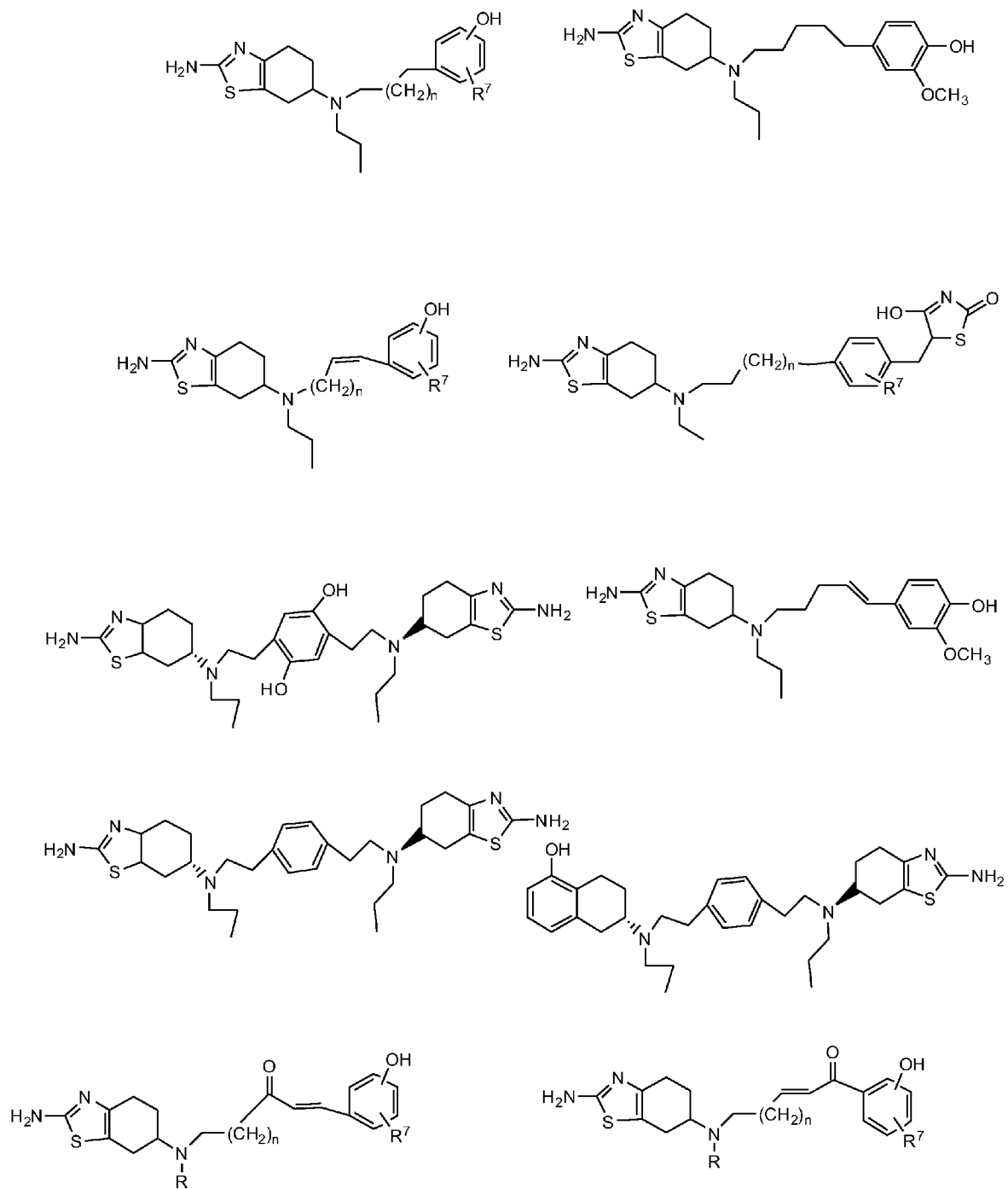

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; all R groups include H, $C_{1-10}$ alkyl, $C_{2-10}$ alkenyl, halo, aryl, heteroaryl, and the like; the first use of a symbol carries through to subsequent uses unless defined to the contrary; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In a variation, the term "organyl group" means any organic substituent group, regardless of functional type, having one free valence at a carbon atom, e.g. methyl, ethyl, propyl, butyl, pyridinyl, 4-pyridylmethyl, and the like.

In a variation, the term "alkyl" means a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

In a variation, the term "alkanediyl" means a straight or branched hydrocarbon diradical having from 1 to 10 carbon atoms formed by removing 2 hydrogen atoms from an alkane.

In a variation, the term "alkoxy" and "thioalkoxy" are O-alkyl or S-alkyl of from 1 to 8 carbon atoms as defined above for "alkyl".

In a variation, the term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

In a variation, the term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

In a variation, the term "alkenediyl" means a straight or branched hydrocarbon diradical having from 2 to 12 carbon atoms formed by removing 2 hydrogen atoms from a $C_{2-12}$ alkene.

In a variation, the term "alkynyl" means a straight or branched triple bonded unsaturated hydrocarbon radical having from 2 to 12 carbon atoms and includes, for example, ethynyl, 2-propynyl, 3-butynyl, 4-pentynyl, 5-hexynyl, 6-heptynyl, 7-octynyl, 8-nonynyl, 9-decynyl, 10-undecynyl, 11-dodecynyl, and the like.

In a variation, the term "alkynediyl" means a straight or branched hydrocarbon diradical having from 2 to 12 carbon atoms formed by removing 2 hydrogen atoms from a $C_{2-12}$ alkyne.

In a variation, the term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like. The term "aryl" means an aromatic radical which is a phenyl group, a phenylalkyl group, a phenyl group substituted by 1 to 4 substituents selected from alkyl as defined above, alkoxy as defined above, thioalkoxy as defined above, halogen, trifluoromethyl, dialkylamino as defined above for alkyl, nitro, cyano, etc.

In a variation, the term "heterocycloalkyl" means a saturated hydrocarbon ring having 3 to 8 carbon atoms in which 1 or more carbon atoms are replaced by N, S, O, Se, etc. Examples includes 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

In a variation, the term "aryl" means an aromatic radical such as a phenyl group, a naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano —$SO_2NH_2$, or nitro, or a naphthyl group substituted by 1 to 4 substituents as defined above for a phenyl group substituted by 1 to 4 substituents.

In a variation, the term "heteroaryl" means a $C_{5-10}$ heteroaromatic radical such as 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from $NH_2$, OH, S, halogen as defined hereinafter, alkyl as defined above, or alkoxy as defined above.

In a variation, the term "halogen" or "halo" means fluorine, chlorine, bromine, or iodine.

Abbreviations:
"h" is hour;
"s" is seconds;
"rt" is room temperature;
"et" is ethyl;
"me" is methyl;
"BOC" is Di-tert-butyl dicarbonate;
"TBDMS" is tert-butyldimethylsilyl;
"THF" is tetrahydrofuran;
"DMSO" is dimethylsulfoxide;
"DMAP" is 4-dimethylaminopyridine;
"TFA" is trifluoroacetic acid;
"DCE" is 1,2-dichloroethane;
"tol" is tolyl;
"DIBALH" is diisobutylaluminium hydride;
"DCM" is dichloromethan;
"DMF" is dimethylformamide;
"TBAF" is tetra-n-butylammonium fluoride;
"NaHMDS" is sodium bis(trimethylsilyl)amide; and
"PCC" is pyridinium chlorochromate.

In at least one embodiment, the present invention provides a compound having formula I for treating a neurodegenerative and other related CNS diseases:

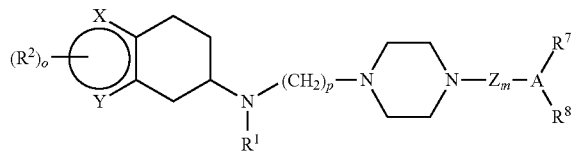

I $R^1$ is a $C_{1-12}$ organyl group, preferably selected from among optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl, each of the foregoing alkyl, alkenyl, alkynyl, cycloalkyl, etc. groups optionally halo substituted, preferably fluoro and/or chloro substituted, or substituted by $C_{1-4}$ alkoxy, $C_{1-8}$ alkoxy $C_{1-4}$ acyloxy, $C_{1-4}$ acyl, —C(O)—$R^4$, or —$R^5$—NH—$SO_2$—$NR^4_r$, —$R^5$—NH—C(O)—$R^4$, —$R^5$—$NR^4_r$, or —$R^5$—Ar where $R^4$ is H or $C_{1-12}$ organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl; and $R^5$ is $C_{1-8}$ alkenyl, and r is 2 or 3, with the proviso that when r is 3, the nitrogen of the $NR^4_r$ group will bear a positive formal charge. When there is a formal charge, the compound includes a suitable negatively charged counter ion such as chloride, bromide, and the like. Ar is a $C_{6-10}$ aryl ring system, preferably a $C_{6-10}$ aryl ring system, optionally including one or more heteroatoms or a $C_{5-10}$ $C_{5-12}$ heteroaryl. Preferably Ar is phenyl, thienyl, pyridyl, biphenyl, or naphthyl each optionally substituted with CN, halo, $C_{1-8}$ alkyl, $C_{2-8}$ alkenyl, $C_{4-8}$ cycloalkyl, $C_{4-8}$ cycloalkenyl, or $C_{6-10}$ aryl;

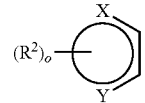

is a $C_{6-12}$ aromatic ring system, $C_{5-12}$ heteroaromatic ring system and/or an optionally heterocyclic ring system containing 5 to 12 ring atoms and up to three heteroatoms individually selected from the group consisting of N, O, S, and Se. When the ring system includes 0 heteroatoms, the ring system is formally a $C_{5-12}$ carbon ring system (e.g., a cycloalkyl). In a refinement, this rings systems are fused to each other or to an aromatic ring. They also are linked together or to an aromatic ring. In another variation, this moiety is an optionally heterocyclic ring system containing 5 or 6 ring atoms and up to three heteroatoms individually selected from the group consisting of N, O, S, and Se. This $C_{6-12}$ aromatic ring system, $C_{5-12}$ heteroaromatic ring system and/or an optionally heterocyclic ring system is optionally substituted by o $R^2$ groups, where o is 0, 1, 2, 3, or 4, the upper limit bounded by the number of available substituent sites. In a variation, X and Y may be N, CH, NR, O, S, and Se where R is hydrogen, alkyl, or aryl;

$R^2$ are $C_{1-12}$ organyl groups. In a variation, $R^2$ are $C_{1-10}$ hydrocarbon groups optionally containing one or more O, N, S, or Se heteroatoms. In another variation, $R^2$ are selected from among $C_{1-4}$ alkyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, $-NR^3_q$ where $R^3$ individually are H or organyl groups. For example, $R^3$ may be H, $C_{1-8}$ alkyl, $C_{1-8}$ alkoxyl, $C_{2-8}$ alkenyl, $C_{2-10}$ alkynyl, $C_{4-8}$ cycloalkyl, $C_{4-8}$ cycloalkenyl, $C_{6-10}$ aryl and q is 2 or 3, with the proviso that when q is 3, the group bears a positive formal charge; $-NH-C(O)-R^3$, $-NH-C(O)-NR^4_2$, and related compounds wherein the hydrocarbon groups in each case may optionally be substituted with $-CN$, $C_{1-4}$ alkyl, $C_{1-8}$ alkyl, $-OR^3$, $-OH$, halo, particularly fluoro and/or chloro, $-CF_3$, and the like. Two $R^2$ may also together form an alicyclic or aromatic fused five or six membered ring, optionally containing heteroatoms O, N, S, or Se. $R^3$ may also be arylsulfonyl, preferably 4-chlorophenylsulfonyl, 3,4-dichlorophenylsulfonyl; 4-(trifluoromethyl)phenylsulfonyl; $X^4-Ar-SO_2$ where $X^4$ is an electron withdrawing or electron donating substituent and Ar is a $C_{6-10}$ aromatic or $C_{5-10}$ heteroaromatic moiety; or keto, preferably phenylketo, 4-(trifluoromethyl)phenylketo, or aceto;

$R^7$, $R^8$ are each independently, hydrogen (H), hydroxyl, oxo (i.e., carbonyl), $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo (e.g. fluoro or chloro), $C_{1-4}$ aldehyde, or $-NR^4_q$, where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl and like groups where $R^4$ is H or $C_{1-12}$ organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl. In a variation, $R^7$, $R^8$ are not hydroxyl;

A is a $C_{6-12}$ aryl group, $C_{5-12}$ heteroaryl group, or an optionally substituted 3-hydroxypyridin-4(1H)-one. In one variation, A contains one or more heteroatoms. In another variation, A may be directly bonded to a nitrogen atom of the piperazinyl group. In still another variation, A is an $C_{6-12}$ group consisting of 1 to 4 rings, may contain heterocyclic rings, optionally fused, optionally linked, and optionally substituted by $C_{1-4}$ alkyl, $C_{1-4}$ alkoxyl, $C_{1-4}$ alkyl, $C_{1-8}$ alkoxyl, $C_{2-4}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, $-NR^4_q$, and like groups where $R^4$ is H or organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl; and q is 2 or 3, with the proviso that when q is 3, the group bears a positive formal charge. It should be noted that unsaturated groups such as alkenyl and cycloalkenyl include multiply unsaturated groups such as alkadienyl and cycloalkadienyl. Alkyl and cycloalkyl groups herein also include aryl-substituted alkyl and cycloalkyl groups, while aryl groups also include alkyl and cycloalkyl-substituted aryl groups. In a variation, A is optionally substituted thienyl, pyridyl, bipyridyl, phenyl, biphenylyl, or naphthyl, more preferably phenyl and biphenyl, quinolone, indole, and isoquinoline. Preferred substituents include $C_{1-4}$ alkyl, $C_{1-8}$ alkyl, $-CN$, halo, $C_{1-8}$ alkoxyl, $C_{1-4}$ alkoxyl, and $NH_2SO_2R^3$, $CF_3$, arylsulfonyl, arylsulfonamide, etc., more preferably o-OCH$_3$, 2,3-dichloro, and p-NHSO$_2$CH$_3$;

p is an integer from 1 to 6; and $Z_m$ is absent or a divalent linking moiety in which Z is repeated m times. Examples of Z include $-CH_2-$, $-CO-$, $-N-CH_2-$ or $-N-CO-$, where m is an integer from 0 to 5. In another variation, m is an integer from 0 to 2. In a refinement, m is 0, 1, 2, 3, 4, or 5 and p is 1, 2, 3, 4, 5, or 6. In a refinement, $Z_m$ is $(CH_2)_n$, $(CH_2)_nCO$, $(CH_2)-NCO(CH_2)_k$, $C_{1-10}$ carboximido, $C_{1-10}$ alkyl (i.e., an $C_{1-10}$ alkanediyl), $C_{2-10}$ alkenyl (i.e., an $C_{2-10}$ alkanediyl), $(CH_2)-CH=CH(CH_2)_k$, $(CH_2)-CC(CH_2)_k$, $C_{2-10}$ alkynyl (i.e., an $C_{2-10}$ alkynediyl), where n and k are integers from 0 to 8;

FIGS. 1-6 provide examples of compound falling within the present embodiment. In these Figures, n is 0 to 8 and more particularly, n is 0, 1, 2, 3, 4, 5, or 6. $R^7$, $R^8$ are as set forth above. In particular, $R^7$, $R^8$ and $R^9$ is hydrogen (H), hydroxyl, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, $-NR^4_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl. The present embodiment provides variations of the compounds set forth in U.S. Pat. No. 20120108815, the entire disclosure of which is hereby incorporated by reference.

A variation of the compounds having formula I are described by formula IA and IB:

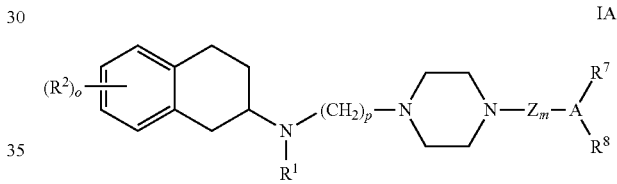

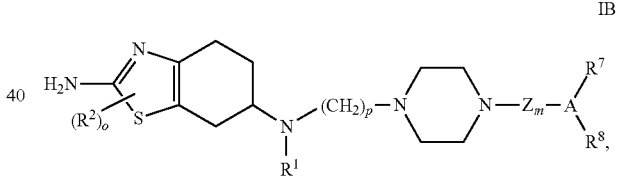

where $R^1$, $R^2$, $R^7$, $R^8$, Z, $Z_m$, m, o, p, X, Y, and A are the same as set forth above.

In another embodiment, a compound having formula II for treating neurodegenerative and other related CNS diseases is provided:

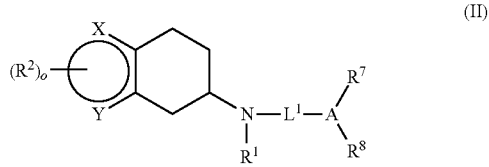

where $R^1$, $R^2$, $R^7$, $R^8$, o, p, X, Y, and A are the same as set forth above. $L^1$ is a linking group. In a refinement, $L^1$ is $(CH_2)_n$, $(CH_2)_nCO$, $(CH_2)_nNCO(CH_2)_k$, $C_{1-10}$ carboximido, $C_{1-10}$ alkyl (i.e., an $C_{1-10}$ alkanediyl), $C_{2-10}$ alkenyl (i.e., an $C_{2-10}$ alkanediyl), $(CH_2)_nCH=CH(CH_2)_k$, $(CH_2)_nCC(CH_2)_k$, $C_{2-10}$ alkynyl (i.e., an $C_{2-10}$ alkynediyl), where n and k are integers from 0 to 8; and $R^7$, $R^8$ each independently, hydrogen (H), hydroxyl, $C_{1-8}$ alkyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, —$NR^4{}_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl. In a refinement, n and k are each independently, 0, 1, 2, 3, 4, 5, 6, 7, and 8.

Figure 11:
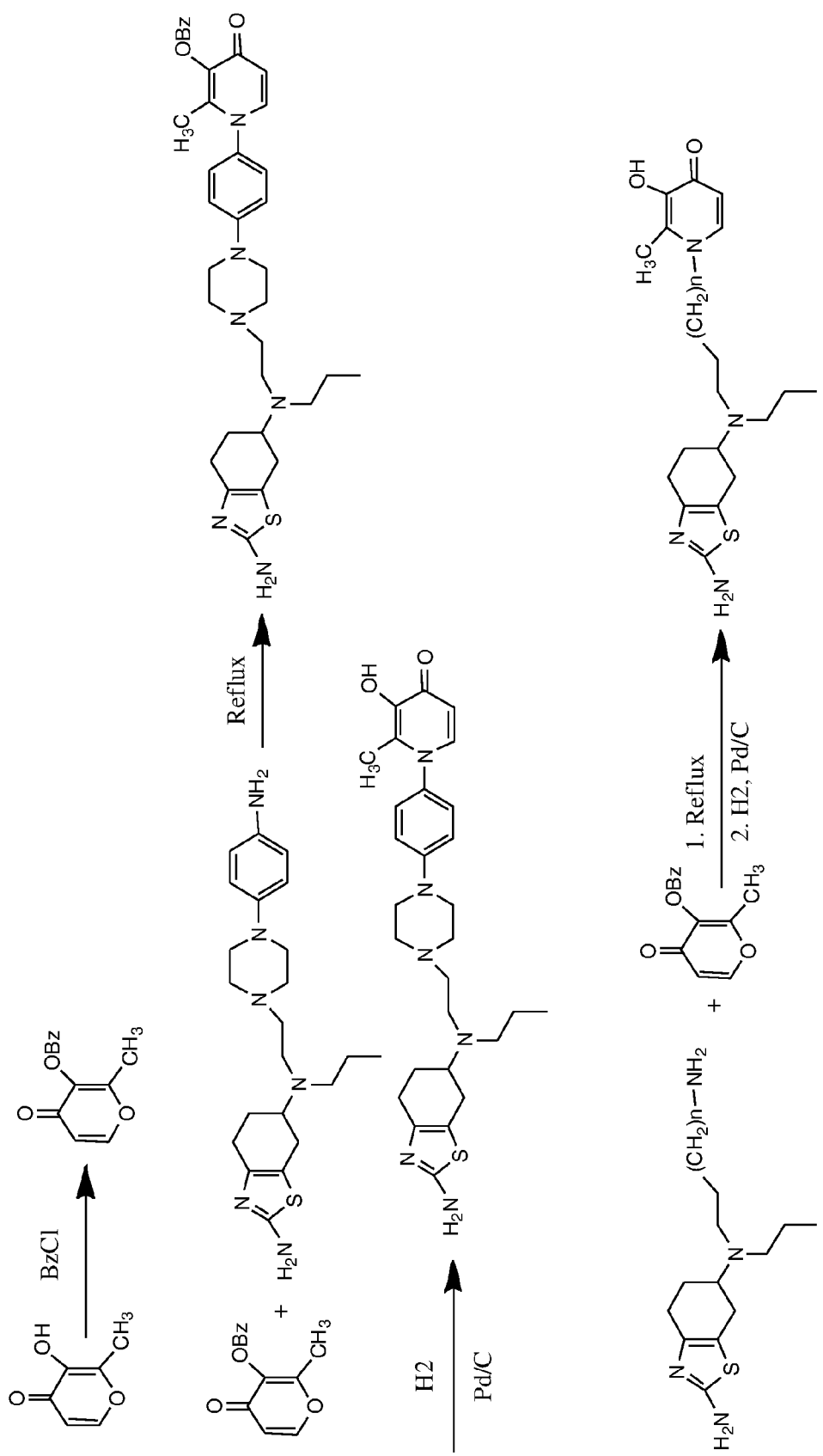
FIG. 11 provides a synthetic scheme for compounds having formula II.

FIGS. 7-10 provide examples of the compounds having formula II while FIG. 11 provides a synthetic scheme. In these Figures, n is 0 to 8 and more particularly, n is 0, 1, 2, 3, 4, 5, or 6. $R^7$, $R^8$ are as set forth above. In particular, $R^7$, $R^8$, $R^9$ is hydrogen (H), hydroxyl, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, —$NR^4{}_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl.

A variation of the compounds having formula II are described by formula IIA and IIB:

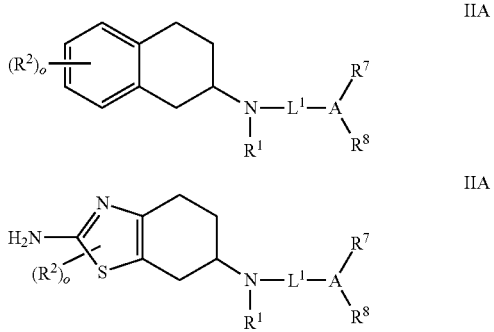

where $R^1$, $R^2$, $R^7$, $R^8$, $L_1$, o, and A are the same as set forth above.

In a refinement of the compounds having formula I, IA, IB, II, IIA, and IIB, A is selected from the group consisting of:

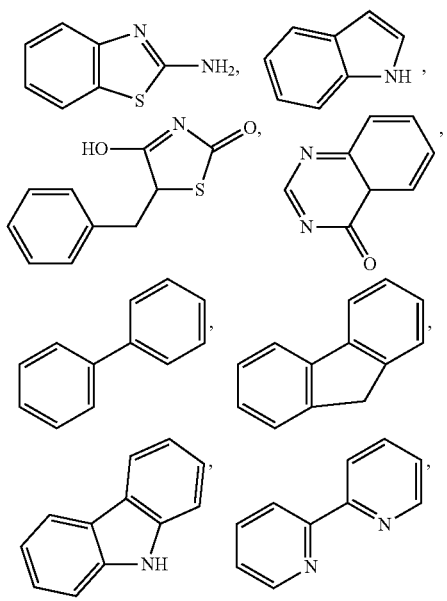

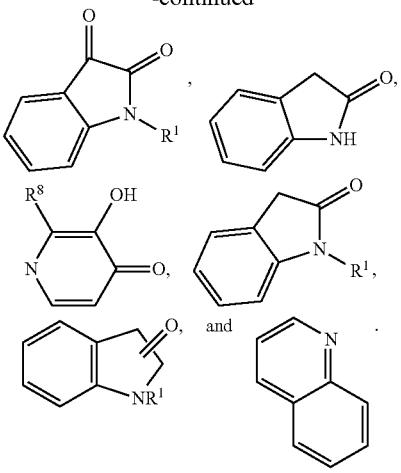

The compounds set forth herein may be used per se or as pharmaceutically acceptable derivatives. The latter term includes salts, esters, and other derivatives generally considered acceptable by pharmaceutical standards. Useful derivatives, for example, include salts of organic and inorganic acids such as sulfates, phosphates, hydrohalide salts, carboxylate salts, etc., as well as esters of carboxylic acid or hydroxyl substituents, ethers of hydroxyl substituents, amides of amino substituents, as well as carbamates, ureas, etc. Synthesis of these derivatives is conventional, and well known to those skilled in pharmaceutical chemistry. For example, compounds bearing hydroxyl groups may be converted to esters by customary techniques of organic chemistry, such as reaction with an acyl halide, carboxylic acid anhydride, or by esterification with an acid while removing byproduct water. In some cases, derivation may be desired to facilitate compounding of the pharmaceutical into an acceptable form such as tablets, powder, aqueous dispersion, capsule, etc., or may be useful in assisting bioavailability of the drug following administration, for example, by rendering the compound more or less soluble. In many cases, such as, for example, esters, ureas, carbamates, ethers, etc., the derivative may act as "prodrug," which liberates the active form by biological transformation, i.e., by enzymatic hydrolysis of an ester functionality, as is well known to the pharmaceutical chemist.

Typical dosages for mammalian species may vary from 0.001 mg/Kg of body weight to about 100 mg/Kg of body weight, preferably 0.01 mg/Kg to 5 mg/Kg. The actual amount will vary depending upon the particular CNS activity desired to be altered, and the desired degree of alteration. The upper limits may, as with virtually all drugs, be limited by toxicity of the drug or its metabolites, or by the presence of unwanted side effects. The drugs may be administered in any form, but preferably in the form of tablets or capsules with appropriate excipients. Dosages, forms of administration, etc., can be readily determined by those skilled in the art.

Guidelines to the effective dosages in mammalian species are provided by the many known drugs commercially available which bind to CNS monoamine receptor sites, and by comparing the binding affinities of these pharmaceuticals with the target compounds of the subject invention by in vivo and in vitro studies. In addition to the utility of the subject invention compounds in treatment of diseases such as Parkinson's disease, schizophrenia, treatment for addiction such as cocaine addiction, and the like, the subject invention compounds are also useful, particularly in their radio labeled form, for clinical studies directed to distribution of monoamine receptor sites in the brain and the effect which compounds, such as cocaine, have on these sites.

FIG. 12 provides a synthetic scheme for making compounds having formula I. The reaction conditions for this scheme are: (a) trisisopropylsilyl chloride, NaH, THF; (b) 4, $PdCl_2(P(o-tol)_3]_2$, NaOtBu, xylenes, reflux; (c) $CF_3COOH$, $CH_2Cl_2$, (d) (2-bromo-ethoxy)-tert-butyl-dimethyl silane, $K_2CO_3$, $CH_3CN$, reflux; (e) $(Boc)_2O$, DMAP, THF; (f) n-$Bu_4NF$, THF; (g) $(COCl)_2$, DMSO, $Et_3N$, $CH_2Cl_2$, −78° C.-rt; (h)(+/−), (−) or (+)-pramipexole, $Na(OAc)3BH$, $CH_2Cl_2$; (i) $CF_3COOH$, $CH_2Cl_2$; (j) 2, $Na(OAc)3BH$, $CH_2Cl_2$; (k) aq. HBr (48%), reflux.

5-Bromo-1-(triisopropylsilyl)-1H-indole (2)

Into a stirring solution of NaH (4.03 g, 170.0 mmol) in dry THF (150 mL), compound 1 (16.44 g, 83.9 mmol) was added portion wise at 0° C. The reaction mixture was allowed to stir at room temperature for 1 h, followed by dropwise addition of triisopropylsilyl chloride (20 g, 103.7 mmol). The reaction mixture was stirred for 12 h and then filtered through celite. The crude residue was purified by column chromatography using hexane as solvent to afford compound 2 (22 g, 75%). $^1$H NMR ($CDCl_3$, 400 MHz): δ 1.23 (s, 18H), 1.74 (heptet, J=7.6 Hz, 3H), 6.64 (d, J=3.2 Hz, 1H), 7.07 (d, J=6 Hz, 1H), 7.14 (s, 1H), 7.31 (d, J=3.2 Hz, 1H), 7.45 (d, J=8.8, 1H).

tert-Butyl 4-(1-(triisopropylsilyl)-1H-indol-5-yl) piperazine-1-carboxylate (3)

A mixture of compound 2 (22.0 g, 63.0 mmol), tert-butyl piperazine-1-carboxylate (11.71 g, 63.0 mmol), $PdCl_2[P(O-tol)_3]_2$ (2.47 g, 3.1 mmol) and NaOtBu (9.08 g, 94.4 mmol) in xylenes (175 mL) was heated at 110° C. for 12 h. The reaction mixture was filtered through celite and concentrated in vacuo. The crude residue was purified by column chromatography (EtOAc/hexane, 1:20) to afford compound 3 (13.22 g, 46%). $^1$H NMR ($CDCl_3$, 400 MHz): δ 1.19 (s, 18H), 1.55 (s, 9H), 1.74 (heptet, J=6.8 Hz, 3H), 3.14 (bs, 4H), 3.67 (bs, 4H), 6.60 (t, J=6 Hz, 1H), 6.94 (d, J=8.8, 1H), 7.19 (s, 1H), 7.26 (t, J=2.8 Hz, 1H), 7.47 (d, J=8.8 Hz, 1H).

Procedure C. 5-Piperazin-1-yl-1H-indole (4)

To a stirring solution of compound 3 (7.70 g, 16.8 mmol) in $CH_2Cl_2$ (15 mL), TFA (15 mL) was added slowly at room temperature and the reaction mixture was stirred for 2 h. Unreacted TFA and solvent were removed under reduced pressure and the salt was washed with diethylether. A saturated solution of $NaHCO_3$ was added to the salt, followed by extraction with $CH_2Cl_2$ (3×50 mL). The combined organic layer was dried over $Na_2SO_4$, filtered and evaporated in vacuo to provide compound 4 (2.88 g, 85%). $^1$H NMR ($CDCl_3$, 400 MHz): δ 1.85 (bs, 1H), 2.80-3.28 (m, 8H), 6.85-7.10 (m, 1H), 7.02-7.40 (m, 4H), 8.31 (bs, 1H).

Procedure D. 5-{4-[2-(tert-Butyl-dimethyl-silanyloxy)ethyl]piperazin-1-yl}-1H-indole (5)

A mixture of compound 4 (2.88 g, 14.3 mmol), (2-bromoethoxy)-tert-butyl-dimethylsilane (3.42 g, 14.3 mmol) and $K_2CO_3$ (5.93 g, 42.9 mmol) in $CH_3CN$ (50 mL) was refluxed for 14 hours. After filtration, acetonitrile was evaporated under reduced pressure and the crude material was purified by silica gel column chromatography (EtOAc/hexane, 3:1) to give compound 5 (4.01 g, 78%). $^1$H NMR ($CDCl_3$, 400 MHz): δ 0.02 (s, 6H), 0.83 (s, 9H), 2.30-2.80 (m, 6H), 2.82-3.30 (m, 4H), 3.52-3.82 (m, 2H), 6.25-6.48 (m, 1H), 6.75-7.30 (m, 4H), 8.09 (s, 1H).

5-{4-[2-(tert-Butyl-dimethyl-silanyloxy)ethyl]piperazin-1-yl}indole-1-carboxylic acid tert-butyl ester (6)

Amine 5 (4.0 g, 11.1 mmol) was reacted with $(Boc)_2O$ (2.68 g, 12.2 mmol) and DMAP (1.49 g, 12.2 mmol) in THF (50 mL) at room temperature using procedure G. The crude material was purified by column chromatography over silica gel (EtOAc/hexane, 1:1) to give compound 6 (5.2 g, ~100%). $^1$H NMR ($CDCl_3$, 400 MHz): δ 0.08 (s, 6H), 0.95 (s, 9H), 1.65 (s, 9H), 2.61 (t, J=6.4 Hz, 2H), 2.73 (t, J=4.8 Hz, 4H), 3.19 (t, J=4.8 Hz, 4H), 3.81 (t, J=6.4 Hz, 2H), 6.47 (d, J=3.6 Hz, 1H), 7.01 (dd, J=6.4, 2.4 Hz, 1H), 7.06 (dd, J=6.4, 2.4 Hz, 1H), 7.53 (s, 1H), 8.00 (s, 1H).

Procedure E. 5-[4-(2-Hydroxy-ethyl)piperazin-1-yl]indole-1-carboxylic acid tert-butyl ester (7)

Into a stirring solution of compound 6 (2.0 g, 4.3 mmol) in THF (30 mL), n-tetrabutylammonium fluoride (1.14 g, 4.3 mmol, 1.0 M solution in THF) was added at 0° C. The reaction mixture was then stirred at room temperature for 1 h. THF was evaporated in vacuo, the residue was diluted with $CH_2Cl_2$ (50 mL) and washed with water. The water layer was extracted with $CH_2Cl_2$ (3×75 mL). The combined organic layer was washed with brine, dried over $Na_2SO_4$, and evaporated. The crude product was purified by silica gel column chromatography (EtOAc/MeOH, 20:1) to yield compound 7 (1.49 g, 99%). $^1$H NMR ($CDCl_3$, 400 MHz): δ 1.65 (s, 9H), 2.61 (t, J=5.2 Hz, 2H), 2.70 (t, J=4.8 Hz, 4H), 3.19 (t, J=4.8 Hz, 4H), 3.67 (t, J=5.2 Hz, 2H), 6.47 (d, J=3.6 Hz, 1H), 7.01 (dd, J=6.8, 2 Hz, 1H), 7.06 (d, J=2 Hz, 1H), 7.53 (s, 1H), 8.00 (s, 1H).

tert-butyl 4-chloro-5-(4-(2-oxoethyl)piperazin-1-yl)-1H-indole-1-carboxylate (8)

Compound 7 (1.49 g, 4.3 mmol) was reacted with oxalyl chloride (0.75 mL, 8.6 mmol), DMSO (1.23 mL, 17.3 mmol) and $Et_3N$ (3.6 mL, 25.8 mmol) in $CH_2Cl_2$ (40 mL) using procedure A. The crude residue was purified by column chromatography using ethyl acetate as solvent to afford compound 8 (1.23 g, 83%).

tert-butyl 5-(4-(2-((2-amino-4,5,6,7-tetrahydrobenzo[d]thiazol-6-yl)(propyl)amino)ethyl)piperazin-1-yl)-4-chloro-1H-indole-1-carboxylate [(±)-9]

Compound 8 (175 mg, 0.51 mmol) was reacted with (±)-pramipexole (108 mg, 0.51 mmol) and $NaBH(OAc)_3$ (194 mg, 0.92 mmol) in $CH_2Cl_2$ (15 mL) according to procedure B. The crude product was purified by silica gel column chromatography (EtOAc/MeOH, 20:1) to yield compound (±)-9 (150 mg, 55%). $^1$H NMR ($CDCl_3$, 400 MHz): δ 0.91 (t, J=6.8 Hz, 1H), 1.35-1.60 (m, 2H), 1.67 (s, 9H), 1.89-2.10 (m, 1H), 2.30-3.30 (m, 20H), 4.94 (bs, 2H), 6.67 (t, J=3.2 Hz, 1H), 7.09 (dd, J=8.8, 2.8 Hz, 1H), 7.28 (dd, J=3.2 Hz, 1H), 7.59 (s, 1H), 7.97 (d, J=6.4 Hz, 1H).

(S)-tert-butyl 5-(4-(2-((2-amino-4,5,6,7-tetrahydrobenzo[d]thiazol-6-yl)(propyl)amino)ethyl)piperazin-1-yl)-4-chloro-1H-indole-1-carboxylate [(−)-9]

Compound 8 (175 mg, 0.51 mmol) was reacted with S-(−)-pramipexole (108 mg, 0.51 mmol) and NaBH(OAc)$_3$ (194 mg, 0.92 mmol) in CH$_2$Cl$_2$ (15 mL) using procedure B. The crude residue was purified by column chromatography (EtOAc/MeOH, 20:1) to afford compound S-(−)-9 (161 mg, 59%). $^1$H NMR (CDCl$_3$, 400 MHz): δ 0.93 (t, J=6.8 Hz, 1H), 1.35-1.60 (m, 2H), 1.68 (s, 9H), 1.89-2.10 (m, 1H), 2.30-3.30 (m, 20H), 4.94 (bs, 2H), 6.67 (t, J=3.2 Hz, 1H), 7.09 (dd, J=8.8, 2.8 Hz, 1H), 7.28 (dd, J=3.2 Hz, 1H), 7.60 (s, 1H), 7.97 (d, J=6.4 Hz, 1H).

(R)-tert-butyl 5-(4-(2-((2-amino-4,5,6,7-tetrahydrobenzo[d]thiazol-6-yl)(propyl)amino)ethyl)piperazin-1-yl)-4-chloro-1H-indole-1-carboxylate [(+)-9]

Compound 8 (175 mg, 0.51 mmol) was reacted with R-(+)-pramipexole (108 mg, 0.51 mmol) and NaBH(OAc)$_3$ (194 mg, 0.92 mmol) in CH$_2$Cl$_2$ (15 mL) using procedure B. The crude residue was purified by column chromatography using (EtOAc/MeOH, 20:1) to afford compound R-(+)-9 (164 mg, 60%). $^1$H NMR (CDCl$_3$, 400 MHz): δ 0.91 (t, J=6.8 Hz, 1H), 1.37-1.60 (m, 2H), 1.67 (s, 9H), 1.89-2.10 (m, 1H), 2.30-3.30 (m, 20H), 4.94 (bs, 2H), 6.67 (t, J=3.2 Hz, 1H), 7.10 (dd, J=8.8, 2.8 Hz, 1H), 7.28 (dd, J=3.2 Hz, 1H), 7.59 (s, 1H), 7.98 (d, J=6.4 Hz, 1H).

N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(±)-10]

Compound (±)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound (±)-10 (106 mg, 38%). $^1$H NMR (CD$_3$OD, 400 MHz): δ 0.99 (t, J=7.2 Hz, 3H), 1.52-1.74 (m, 2H), 1.76-2.04 (m, 1H), 2.19 (d, J=9.2 Hz, 1H), 2.52-2.84 (m, 6H), 3.10-3.58 (m, 13H), 6.50 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.0, 22.2, 24.0, 25.1, 47.0, 51.1, 54.4, 54.8, 59.2, 101.4, 101.5, 111.8, 115.3, 116.1, 127.8, 129.7, 135.1, 136.0, 140.7, 171.0. M.p. 110-115° C. Anal. calculated for C$_{30}$H$_{40}$F$_9$N$_6$O$_{7.5}$S: C, H, N.

(S)—N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(−)-10]

Compound (−)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound S-(−)-10 (120 mg, 43%). $^1$H NMR (CD$_3$OD, 400 MHz): δ 0.98 (t, J=7.2 Hz, 3H), 1.54-1.74 (m, 2H), 1.76-2.04 (m, 1H), 2.19 (d, J=9.2 Hz, 1H), 2.52-2.84 (m, 6H), 3.10-3.58 (m, 13H), 6.51 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.0, 22.3, 24.0, 25.1, 47.0, 51.1, 54.5, 54.8, 59.2, 101.4, 101.6, 111.8, 115.3, 116.1, 127.8, 129.7, 135.1, 136.0, 140.8, 171.0. [α]$^{25}_D$=−11.0° (c=1.0, CH$_3$OH). M.p. 115-120° C. Anal. calculated for C$_{31}$H$_{37.5}$F$_{10.5}$N$_6$O$_7$S: C, H, N.

(R)—N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(+)-10]

Compound (+)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound R-(+)-10 (140 mg, 50%). $^1$H NMR (CD$_3$OD, 400 MHz): δ 0.98 (t, J=7.2 Hz, 3H), 1.54-1.78 (m, 2H), 1.76-2.04 (m, 1H), 2.20 (d, J=9.2 Hz, 1H), 2.52-2.84 (m, 6H), 3.10-3.58 (m, 13H), 6.51 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.2, 22.3, 24.0, 25.1, 47.0, 51.2, 54.5, 54.8, 59.2, 101.4, 101.6, 111.8, 115.3, 116.1, 127.8, 129.7, 135.1, 136.2, 140.8, 171.0. [α]$^{25}_D$=−15.5° (c=1.0, CH$_3$OH). M.p. 115-120° C. Anal. calculated for C$_{31}$H$_{37.9}$F$_{10.5}$N$_6$O$_{7.2}$S: C, H, N.

tert-butyl 4-chloro-5-(4-(2-((5-methoxy-1,2,3,4-tetrahydronaphthalen-2-yl)(propyl)amino)ethyl)piperazin-1-yl)-1H-indole-1-carboxylate (11)

Aldehyde 8 (320 mg, 0.93 mmol) was reacted with 5-methoxy-N-propyl-1,2,3,4-tetrahydronaphthalen-2-amine (204 mg, 0.93 mmol) and NaBH(OAc)$_3$ (355 mg, 1.68 mmol) in CH$_2$Cl$_2$ (20 mL) using procedure B. The crude material was purified by column chromatography over silica gel (EtOAc/hexane, 1:1) to give compound 11 (190 mg, 38%). $^1$H NMR (CDCl$_3$, 400 MHz): δ 0.91 (t, J=7.2 Hz, 3H), 1.33-1.75 (m, 13H), 1.95-2.13 (m, 1H), 2.35-3.23 (m, 18H), 3.81 (s, 3H), 6.55-6.77 (m, 3H), 7.03-7.15 (m, 3H), 7.58 (d, J=2.4 Hz, 1H), 7.96 (d, J=6.8 Hz, 1H).

6-((2-(4-(4-chloro-1H-indol-5-yl)piperazin-1-yl)ethyl)(propyl)amino)-5,6,7,8-tetrahydronaphthalen-1-ol (12)

A mixture of compound 11 (60 mg, 0.11 mmol) and 48% aq. HBr (10 ml) was refluxed for 5 h. The reaction mixture was evaporated to dryness and the residue was washed with diethylether. Finally, the HBr salt was recrystallized from ethanol to furnish compound 12 (50 mg, 60%). $^1$H NMR (CD$_3$OD, 400 MHz): δ 0.95 (t, J=7.2 Hz, 3H), 1.41-1.57 (m, 3H), 2.00-2.22 (m, 1H), 2.58-3.18 (m, 19H), 6.61 (d, J=8 Hz, 1H), 6.75 (d, J=8 Hz, 1H), 7.08 (t, J=7.6 Hz, 1H), 7.19-7.38 (m, 3H), 7.51 (d, J=8 Hz, 1H), 7.90 (d, J=8.2 Hz, 1H), 8.50 (bs, 1H). M.p. 250-260° C. Anal. calculated for C$_2$H$_{41.4}$Br$_4$N$_4$O$_{1.7}$: C, H, N.

TABLE 1

Inhibition constants for competition with [$^3$H]spiroperidol binding to cloned rat D2L and D3 receptors expressed in HEK-293 cells.

| Compound | K$_i$ (nM), rD2L [$^3$H]spiroperidol | K$_i$ (nM), rD3 [$^3$H]spiroperidol | D2L/D3 |
|---|---|---|---|
| (±)-10 | 46.7 ± 6.6 | 1.92 ± 0.38 | 24.3 |
| (−)-10 | 39 ± 5 | 2.19 ± 0.39 | 17.8 |
| (+)-10 | 134 ± 12 | 15.9 ± 3.6 | 8.46 |
| 12 | 76.4 ± 2.4 | 10.4 ± 1.6 | 7.3 |

Figure 13:
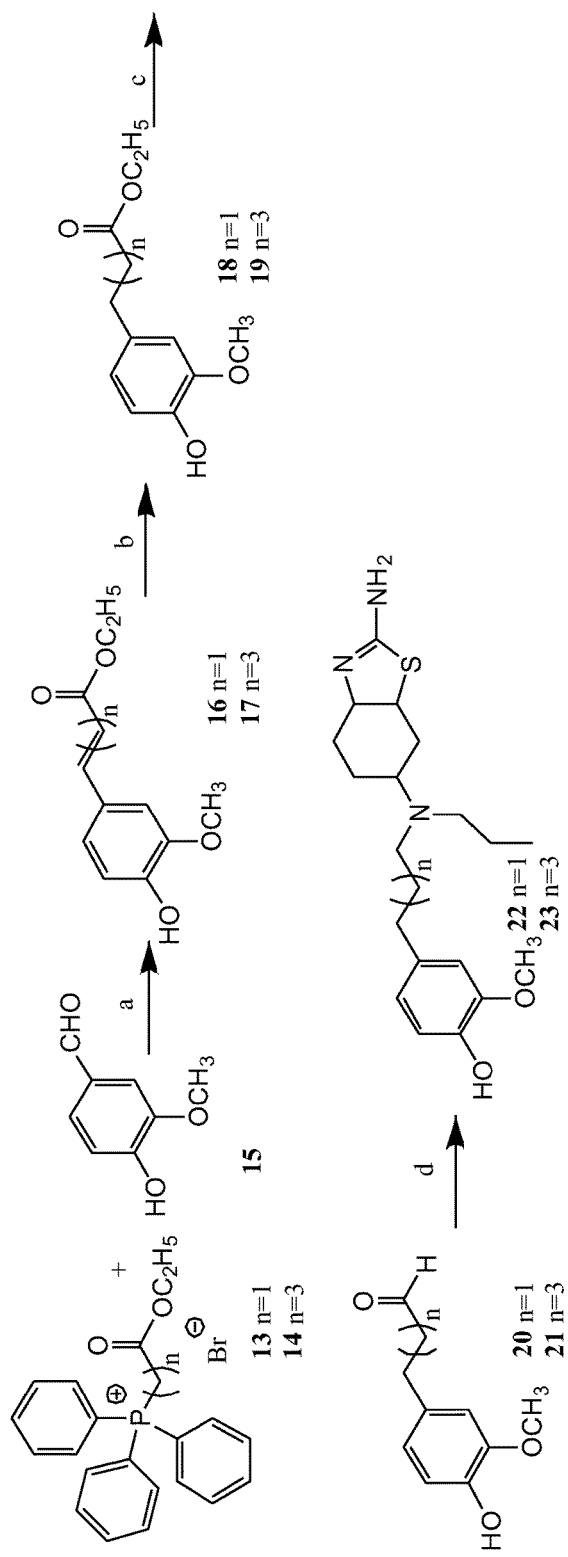
FIG. 13 provides a synthetic scheme for compounds having formula II.

FIG. 13 provides a synthetic scheme for the compounds having formula II. The reaction conditions for this scheme are: (a) NaHMDS, THF, −78° C. to rt, 48 h; (b) 10% pd/C, H$_2$, ethanol, rt, 2 h; (c) DIBALH, toluene, −78° C., 2 h; (d) Pramipexole, NaBH(OAc)$_3$, DCE, rt, 24 h.

Procedure A

Ethyl 3-(4-hydroxy-3-methoxyphenyl)acrylate (16) and Ethyl 5-(4-hydroxy-3-methoxyphenyl)pent-4-enoate (17)

Commercially available (ethoxycarbonylmethyl)triphenylphosphonium bromide 13 (3.10 g, 7.23 mmol) was added to dry THF (8 mL) in an oven-dried round bottom flask. The resulting suspension was cooled to −78° C. Then a solution of NaHMDS (1M in THF, 7.88 mL, 7.88 mmol) was added drop-wise and the reaction mixture stirred at −78° C. for 1 h. Thereafter, a solution of Vanillin 15 (1.0 g, 6.57 mmol) in dry THF (2 mL) was added drop-wise and reaction stirred at −78° C. for 2 h, then warmed to room temperature and stirred for 48 h. The reaction mixture was then extracted with ethyl acetate (2×75 mL) and washed with brine. The combined organic layer was dried over sodium sulfate and concentrated in vacuo. The crude thus obtained was purified by column chromatography (Hexane/ethyl acetate 9:1) to yield compound 16 (1.25 g, 85%) as colorless oil with a preferential Z:E ratio of >20:1: $^1$H NMR (400 MHz, CDCl$_3$) δ ppm 1.33 (t, 3H, J=7.6 Hz, CH$_3$), 3.92 (s, 3H, OCH$_3$), 4.25 (q, 2H, J=7.2 Hz, OCH$_2$), 5.83 (m, 1H, CH), 6.29 (d, 1H, J=15.2 Hz, CH), 6.91 (d, 1H, J=8.0 Hz, ArH), 7.03 (m, 2H, ArH)

Preparation of starting material [3-(Ethoxycarbonyl)propyl]triphenylphosphonium bromide (14)

Triphenylphosphine (3.76 g, 14.35 mmol) and ethyl 4-bromobutyrate (2 g, 10.25 mmol) were added to a dried round bottom flask under argon. The reaction mixture was heated to 120° C. under condenser for 16 h after which the reaction was allowed to come to room temperature. DCM (10 mL) was added, followed by diethyl ether until no further precipitation of product was observed. The precipitate was further washed with ether (100 mL) and solvent dried in vacuo to give pure compound 14 as a white solid (4.64 g) in quantitative yields. $^1$H NMR (400 MHz, CDCl$_3$) δ ppm 1.22 (t, 3H, J=7.2 Hz, CH$_3$), 1.88-1.94 (m, 2H, CH$_2$), 2.86-2.89 (m, 2H, CH$_2$), 3.98-4.12 (m, 4H, CH$_2$), 7.67-7.90 (15H, ArH).

Starting material 14 (3.30 g, 7.23 mmol) was reacted with vanillin 15 (1.0 g, 6.57 mmol) according to procedure A and the crude product was purified using column chromatography (Hexane/ethyl acetate 9:1) to yield compound 17 (1.17 g, 71%) as colorless oil with a preferential Z:E ratio of >20:1: $^1$H NMR (400 MHz, CDCl$_3$) δ ppm 1.24 (t, 3H, J=7.2 Hz, CH$_3$), 2.45 (t, 2H, J=8.0 Hz, CH$_2$), 2.63-2.69 (m, 2H, CH$_2$), 3.88 (s, 3H, OCH$_3$), 4.13 (q, 2H, J=7.2 Hz, OCH$_2$), 5.49-5.55 (m, 1H, CH), 5.64 (s, 1H, OH), 6.37 (d, 1H, J=11.2 Hz, CH), 6.79-6.82 (m, 2H, ArH), 6.88 (d, 1H, J=8.2 Hz, ArH)

Procedure B

Ethyl 3-(4-hydroxy-3-methoxyphenyl)propanoate (18) and Ethyl 5-(4-hydroxy-3-methoxyphenyl)pentanoate (19)

Intermediate 16 (1.0 g, 4.45 mmol) was dissolved in ethanol (10 mL) in a round bottom flask and 10% Pd/C (0.10 g, 10 wt %) was added to it. The reaction flask was degassed and then stirred under hydrogen atmosphere for 2 h at room temperature. After the completion of reaction, the mixture was diluted with ethanol (20 mL) and passed through a short bed of celite. The organic layer was concentrated to afford compound 18 (0.95 gm) as colorless oil in quantitative yield which was pure enough for the next step. $^1$H NMR (400 MHz, CDCl$_3$) δ ppm 1.23 (t, 3H, J=7.2 Hz, CH$_3$), 2.58 (t, 2H, J=8.0 Hz, CH$_2$), 2.87 (t, 2H, J=7.6 Hz, CH$_2$), 3.84 (s, 3H, OCH$_3$), 4.12 (q, 2H, J=7.2 Hz, OCH$_2$), 6.68 (m, 2H, ArH), 6.82 (d, 1H, J=7.2 Hz, ArH).

Intermediate 17 (1.0 g, 3.96 mmol) was stirred under hydrogen atmosphere following procedure B to yield compound 19 (0.98 g) in quantitative yield which was taken to the next step without further purification. $^1$H NMR (400 MHz, CDCl$_3$) δ ppm 1.24 (t, 3H, J=7.2 Hz, CH$_3$), 1.58-1.70 (m, 4H, CH$_2$), 2.31 (t, 2H, J=7.2 Hz, CH$_2$), 2.55 (t, 2H, J=7.2 Hz, CH$_2$), 3.87 (s, 3H, OCH$_3$), 4.12 (q, 2H, J=7.2 Hz, OCH$_2$), 6.65-6.67 (m, 2H, ArH), 6.82 (d, 1H, J=8.0 Hz, ArH)

Procedure C

3-(4-Hydroxy-3-methoxyphenyl)propanal (20) and 5-(4-Hydroxy-3-methoxyphenyl)pentanal (21)

To a solution of compound 18 (0.60 g, 2.67 mmol) in dry toluene (10 mL) under argon was added DIBALH solution (1M in hexane, 2.93 mL, 2.93 mmol) at −78° C. The reaction mixture was stirred at −78 C for 2 h. Methanol (0.20 mL) was added to the reaction mixture and reaction allowed to come to 0° C. The reaction mixture was then added to a separating funnel containing HCl (1N, 10 ml) and extracted with ethyl acetate (3×30 mL). The combined organic layer was washed with brine, dried over sodium sulfate, and evaporated under reduced pressure. The crude was purified by column chromatography (Hexane/ethyl acetate 7:1) to give compound 20 (0.22 gm, 45.6%) as yellow oil. $^1$H NMR (400 MHz, CDCl$_3$) δ ppm 2.75 (t, 2H, J=8.0 Hz, CH$_2$), 2.89 (t, 2H, J=7.6 Hz, CH$_2$), 3.87 (s, 3H, OCH$_3$), 6.68 (m, 2H, ArH), 6.83 (d, 1H, J=7.2 Hz, ArH), 9.81 (t, 1H, J=1.6 Hz, CHO)

Intermediate 19 (0.50 g, 1.96 mmol) was reduced with DIBALH solution (1M in hexane, 2.16 mL, 2.16 mmol) in dry toluene using procedure C. The crude was purified by column chromatography (Hexane/ethyl acetate 8:1) to yield compound 21 (0.196 g, 48%) as colorless oil. $^1$H NMR (400 MHz, CDCl$_3$) δ ppm 1.59-1.68 (m, 4H, CH$_2$), 2.44 (td, 2H, J$_1$=6.40 Hz, J$_2$=1.60 Hz CH$_2$), 2.56 (t, 2H, J=7.2 Hz, CH$_2$), 3.87 (s, 3H, OCH$_3$), 6.65 (m, 2H, ArH), 6.82 (d, 1H, J=8.0 Hz, ArH), 9.75 (t, 1H, J=1.6 Hz, CHO).

Procedure D

4-(3-((2-Amino-4,5,6,7-tetrahydrobenzo[d]thiazol-6-yl)(propyl)amino)propyl)-2-methoxyphenol (22) and 4-(5-((2-Amino-4,5,6,7-tetrahydrobenzo[d]thiazol-6-yl)(propyl)amino)pentyl)-2-methoxyphenol (23)

Into a stirring solution of (±) Pramipexole (0.123 g, 0.58 mmol) in DCE (15 mL) was added aldehyde 20 (0.10 g, 0.55 mmol) and the mixture stirred for 1 h. NaBH(OAC)$_3$ (0.235 g 1.10 mmol) was then added portion-wise and the reaction stirred for 24 h at room temperature. The reaction mixture was quenched with a saturated NaHCO$_3$ solution at 0° C. and extracted with ethyl acetate (3×25 mL). The combined organic layer was dried over sodium sulfate and solvent was removed under reduced pressure. The crude product was purified by column chromatography (ethyl acetate/methanol 20:1) to give compound 22 (0.079 g, 38%). $^1$H NMR (400 MHz, CD$_3$OD) δ ppm 0.95 (t, 3H, J=7.2 Hz, CH$_3$), 1.59 (m, 2H, CH$_2$), 1.81-1.92 (m, 3H, CH$_2$), 2.05-2.12 (m, 1H, CH$_2$), 2.57-2.67 (m, 6H, CH$_2$), 2.73-2.89 (m, 5H, CH$_2$, CH), 3.82 (s, 3H, OCH$_3$), 6.64 (d, 1H, J=8.0 Hz, ArH), 6.71 (d, 1H, J=8.0 Hz, ArH), 6.79 (s, 1H, ArH). The free base was converted into its corresponding hydrochloride salt. Mp 220-222° C. Anal. (C$_{20}$H$_{32}$Cl$_2$N$_3$O$_{2.5}$S) C, H, N.

Aldehyde 21 (0.10 g, 0.48 mmol) and (±) Pramipexole (0.106 g, 0.50 mmol) in DCE (15 mL) were reacted using procedure D and the resulting crude was purified by column chromatography (ethyl acetate/methanol 21:1) to give compound 23 (0.068 g, 35%). $^1$H NMR (400 MHz, DMSO-d$_6$) δ ppm 0.89 (t, 3H, J=7.2 Hz, CH$_3$), 1.28-1.36 (m, 3H, CH$_2$), 1.48-1.53 (m, 4H, CH$_2$), 1.59-1.70 (m, 3H, CH$_2$), 2.57-2.67 (m, 1H, CH$_2$), 2.503-2.65 (m, 9H, CH$_2$), 3.05 (bs, 1H, CH), 3.82 (s, 3H, OCH$_3$), 6.58 (d, 1H, J=8.4 Hz, ArH), 6.64-6.72 (m, 2H, ArH). The free base was converted into its corresponding hydrochloride salt. Mp 224-226° C. Anal. (C$_{23.6}$H$_{37.8}$N$_3$O$_{2.8}$S$_{1.22}$) C, H, N.

Elemental analysis report of compounds 22 and 23

| Compound | Calculated | | | Found | | |
|---|---|---|---|---|---|---|
| | C | H | N | C | H | N |
| 22. 2HCl•0.5H$_2$O | 52.51 | 7.05 | 9.19 | 52.12 | 7.19 | 8.83 |
| 23. 2HCl•0.58C$_2$H$_5$OH•0.22CH$_3$SOCH$_3$ | 54.47 | 7.71 | 8.07 | 54.86 | 7.31 | 7.60 |

Figure 14:
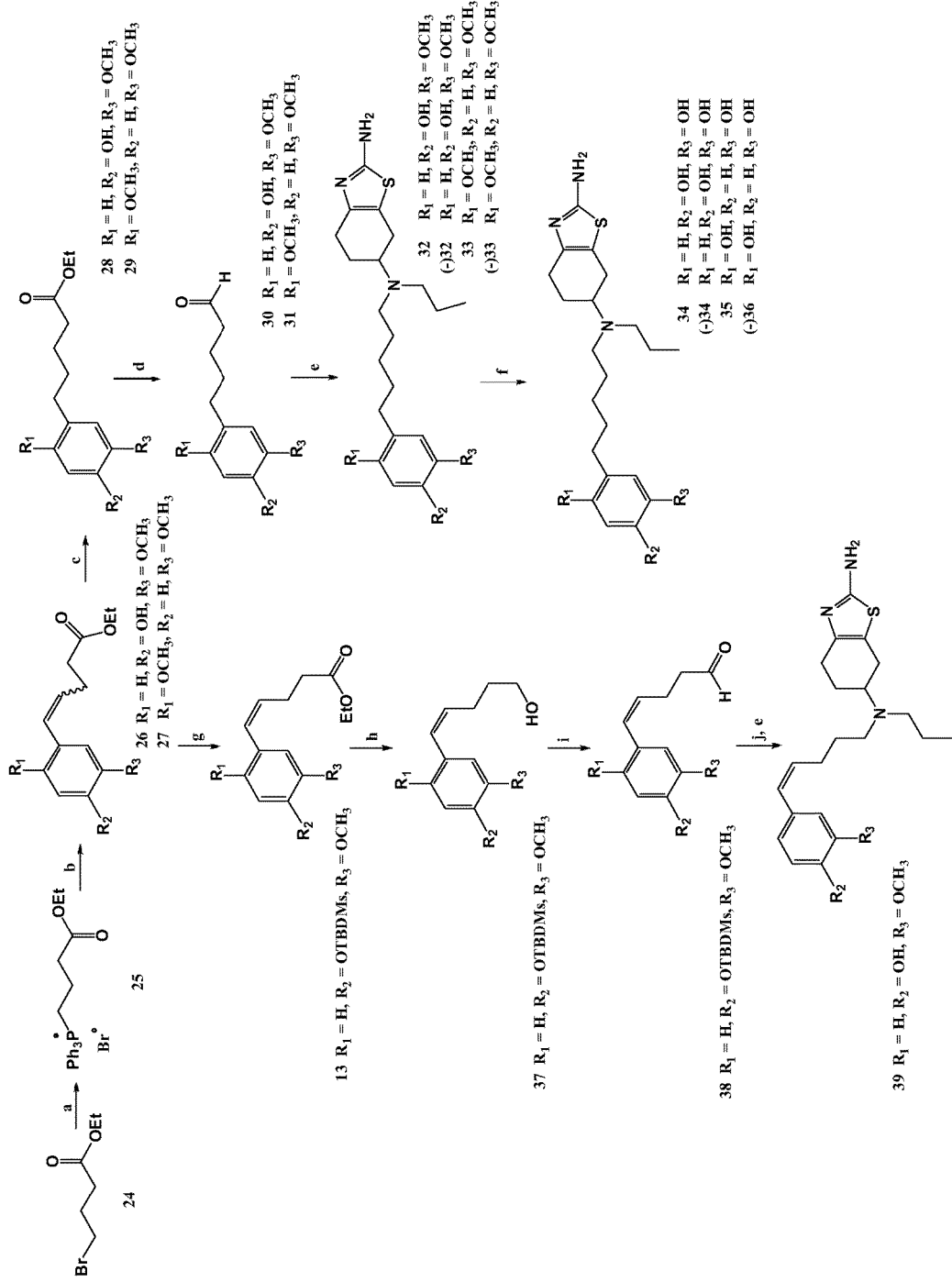
FIG. 14 provides a synthetic scheme for compounds having formula II.

FIG. 14 provides a synthetic scheme for the compounds having formula II, specifically compounds 34, 35, and 35. The reaction conditions for this scheme are (a) TPP, toluene, reflux, 16 h, qunat. yield; (b) Aldehyde, NaHMDS, THF, −78° C. to rt, 48 h; 35-43%; (c) 10% pd/C, H$_2$, ethanol, rt, 2 h, 96%; (d) DIBALH, toluene, −78° C., 2 h, 48-80%; (e) Pramipexole, NaBH(OAc)$_3$, DCM, rt, 36 h, 53-69%; (f) BBr$_3$, DCM, −78° C. to rt, 6 h, 62-80%; (g) TBDMSCl, imidazole, DMF, rt, 2 h, qunat. yield; (h) DIBALH, THF, −10° C. to rt, 6 h, 87%; (i) PCC, DCM, ° C. to rt, 9 h, 45%; (j) TBAF, THF, 0° C., 1.5 h.

[3-(Ethoxycarbonyl)propyl]triphenylphosphonium bromide (25)

Procedure A'.
(4-ethoxy-4-oxobutyl)triphenylphosphonium bromide

Triphenylphosphine (3.76 g, 14.35 mmol) and ethyl 4-bromobutyrate (2 g, 10.25 mmol) was added to a dried round bottom flask under argon. The reaction mixture was heated to 120° C. under condenser for 16 h after which the reaction was allowed to come to room temperature. DCM (10 mL) was added, followed by diethyl ether until no further precipitation of product was observed. The precipitate was further washed with ether (100 mL) and solvent dried in vacuo to give pure compound 25 as a white solid (4.64 g) in quantitative yields. $^1$H NMR (400 MHz, CDCl$_3$) δ ppm 7.67-7.90 (m, 15H), 3.98-4.12 (m, 4H), 2.86-2.89 (m, 2H), 1.88-1.94 (m, 2H), 1.22 (t, J=7.2 Hz, 3H).

Procedure B'. Ethyl 5-(4-hydroxy-3-methoxyphenyl)pent-4-enoate (26)

Starting material 2 (6.61 g, 14.46 mmol) was added to dry THF (15 mL) in an oven-dried round bottom flask. The resulting suspension was cooled to −78° C. Then a solution of NaHMDS (1M in THF, 15.77 mL, 15.77 mmol) was added drop-wise and the reaction mixture stirred at −78° C. for 1 h. Thereafter, a solution of Vanillin (2.0 g, 13.14 mmol) in dry THF (5 mL) was added drop-wise and reaction stirred at −78° C. for 2 h, then warmed to room temperature and stirred for 48 h. The reaction mixture was then extracted with ethyl acetate (2×100 mL) and washed with brine. The combined organic layer was dried over sodium sulfate and concentrated in vacuo. The crude thus obtained was purified by column chromatography using 10% ethyl acetate in hexane to yield compound 26 (1.17 g, 35.6%) as colorless oil with a preferential Z:E ratio of >20:1: $^1$H NMR (400 MHz, CDCl$_3$) δ ppm 6.88 (d, J=8.2 Hz, 1H), 6.79-6.82 (m, 2H), 6.37 (d, J=11.2 Hz, 1H), 5.64 (s, 1H), 5.49-5.55 (m, 1H), 4.13 (q, J=7.2 Hz, 2H), 3.88 (s, 3H), 2.63-2.69 (m, 2H), 2.45 (t, J=8.0 Hz, 2H), 1.24 (t, J=7.2 Hz, 3H).

Ethyl 5-(2,5-dimethoxyphenyl)pentanoate (27)

Starting material 25 (7.56 g, 16.57 mmol) was reacted with 2,5-dimethoxy benzaldehyde (2.5 g, 15.07 mmol) in presence of NaHMDS 1M in THF (18.05 mmol, 18.05 mL) according to Procedure A'. the crude was purified by column chromatography using 7-10% ethyl acetate in hexanes to give compound 27 (1.71 g, 43%). $^1$H NMR (400 MHz, CDCl$_3$) δ ppm 6.82 (d, J=2.4 Hz, 1H), 6.74-6.79 (m, 2H), 6.52 (d, J=11.2 Hz, 1H), 5.65-5.72 (m, 1H), 4.12 (q, J=7.2 Hz, 2H), 3.78 (s, 3H), 3.77 (s, 3H), 2.55-2.60 (m, 2H), 2.41 (t, J=7.2 Hz, 2H), 1.23 (t, J=7.2 Hz, 3H).

Procedure C'. Ethyl 5-(4-hydroxy-3-methoxyphenyl)pentanoate (5)

Intermediate 26 (1.0 g, 3.96 mmol) dissolved in ethanol (10 mL) in a round bottom flask and 10% Pd/C (0.10 g, 10 wt %) was added to it. The reaction flask was degassed and then stirred under hydrogen atmosphere for 2 h at room temperature. After the completion of reaction, the mixture was diluted with ethanol (20 mL) and passed through a short bed of celite. The organic layer was concentrated to afford compound 5 (0.98 gm) in quantitative yield which was pure enough for the next step. $^1$H NMR (400 MHz, CDCl$_3$) δ ppm 6.82 (d, J=8.0 Hz, 1H), 6.65-6.67 (m, 2H), 4.12 (q, J=7.2 Hz, 2H), 2.55 (t, J=7.2 Hz, 2H), 3.87 (s, 3H), 2.31 (t, J=7.2 Hz, 2H), 1.58-1.70 (m, 4H), 1.24 (t, J=7.2 Hz, 3H).

Ethyl 5-(2,5-dimethoxyphenyl)pentanoate (29)

Intermediate 27 (1.0 g, mmol) dissolved in ethanol (10 mL) and reacted with 10% Pd/C (0.1 g, 10 wt %) according to Procedure C' to afford compound 6 (0.96 g, 96%) which was used without further purification. $^1$H NMR (400 MHz, CDCl$_3$) δ ppm 6.75 (d, J=8.8 Hz, 1H), 8.72 (d, J=3.2 Hz, 1H), 6.68 (dd, J=8.4, 2.4 Hz, 1H), 4.12 (q, J=7.2 Hz, 2H), 3.76 (s, 3H), 3.75 (s, 3H), 2.60 (t, J=7.4 Hz, 2H), 2.33 (t, J=7.2 Hz, 2H), 1.56-1.70 (m, 4H), 1.24 (t, J=7.2 Hz, 3H).

Procedure D'.
5-(4-Hydroxy-3-methoxyphenyl)pentanal (30)

To a solution of compound 5 (0.50 g, 1.96 mmol) in dry toluene (10 mL) under argon was added DIBALH solution (1M in hexane, 2.16 mL, 2.16 mmol) at −78° C. The reaction mixture was stirred at −78 C for 2 h. Methanol (0.20 mL) was added to the reaction mixture and reaction allowed to come to 0° C. The reaction mixture was then added to a separating funnel containing HCl (1N, 10 ml) and extracted with ethyl acetate (3×30 mL). The combined organic layer was washed with brine, dried over sodium sulfate, and evaporated under reduced pressure. The crude was purified by column chromatography using 11-15% ethyl acetate in hexanes to yield compound 30 (0.196 g, 48%) as colorless oil. $^1$H NMR (400 MHz, CDCl$_3$) δ ppm 9.75 (t, J=1.6 Hz, 1H), 6.82 (d, J=8.0 Hz, 1H), 6.65 (m, 2H), 3.87 (s, 3H), 2.56 (t, J=7.2 Hz, 2H), 2.44 (td, J$_1$=6.40 Hz, J$_2$=1.60 Hz 2H), 1.59-1.68 (m, 4H).

5-(2,5-dimethoxyphenyl)pentanal (31)

Intermediate 29 (0.6 g, 2.25 mmol) was reduced with DIBALH solution (1M in hexane, 2.47 mL, 2.47 mmol) in dry toluene (10 mL) using procedure D'. The crude was purified by column chromatography using 11-15% ethyl acetate in hexanes to give compound 8 (0.4 gm, 80%) as yellow oil. $^1$H NMR (400 MHz, CDCl$_3$) δ ppm 9.74 (d, J=1.6 Hz, 1H), 6.76 (d, J=8.8 Hz, 1H), 6.67-6.71 (m, 2H), 3.76 (s, 3H), 3.75 (s, 3H), 2.60 (t, J=6.4 Hz, 2H), 2.44 (t, J=6.8 Hz, 2H), 1.58-1.37 (m, 4H).

Procedure E'. 4-(5-((2-Amino-4,5,6,7-tetrahydrobenzo[d]thiazol-6-yl)(propyl)amino)pentyl)-2-methoxyphenol (32)

Into a stirring solution of (±) Pramipexole (015 g, 0.71 mmol) in DCM (8 mL) was added aldehyde 30 (0.148 g, 0.71 mmol) and the mixture stirred for 1 h. NaBH(OAc)$_3$ (0.27 g, 1.27 mmol) was then added portion-wise followed by MeOH (0.8 mL). The reaction was stirred for 36 h at room temperature. The reaction mixture was quenched with a saturated NaHCO$_3$ solution at 0° C. and extracted with DCM (3×25 mL). The combined organic layer was dried over sodium sulfate and solvent was removed under reduced pressure. The crude product was purified by column chromatography using 5-7% MeOH in DCM to give compound 32 (0.2 g, 69%). $^1$H NMR (400 MHz, DMSO-d$_6$) δ ppm 6.64-6.72 (m, 2H), 6.58 (d, J=8.4 Hz, 1H), 3.82 (s, 3H), 3.05 (bs, 1H), 2.50-2.67 (m, 10H), 1.59-1.70 (m, 3H), 1.48-1.53 (m, 4H), 1.28-1.36 (m, 3H), 0.89 (t, J=7.2 Hz, 3H). The free base was converted into its corresponding hydrochloride salt. Mp 224-226° C. Anal. (C$_{23.6}$H$_{37.8}$N$_3$O$_{2.8}$S$_{1.22}$) C, H, N.

(R)-4-(5-((2-Amino-4,5,6,7-tetrahydrobenzo[d]thiazol-6-yl)(propyl)amino)pentyl)-2-methoxyphenol (−32)

Aldehyde 30 (0.148 g, 0.71 mmol), (−) Pramipexole (0.15 g, 0.71 mmol), and NaBH(OAc)$_3$ (0.27 g, 1.27 mmol) in DCM (8 mL) and MeOH (0.8 mL) were reacted using procedure D' and the resulting crude was purified by column chromatography using 5-7% MeOH in DCM to give compound (−32) (0.19 g, 66%). $^1$H NMR (400 MHz, DMSO-d$_6$) δ ppm 6.64-6.72 (m, 2H), 6.58 (d, J=8.4 Hz, 1H), 3.82 (s, 3H), 3.05 (bs, 1H), 2.65-2.67 (m, 1H), 2.50-2.65 (m, 9H), 1.59-1.70 (m, 3H), 1.48-1.53 (m, 4H), 1.28-1.36 (m, 3H), 0.90 (t, J=7.2 Hz, 3H). The free base was converted into its corresponding hydrochloride salt. Mp 196-198° C. Anal. (C$_{22}$H$_{37}$N$_3$Cl$_2$O$_3$S) C, H, N.

N$^6$-(5-(2,5-dimethoxyphenyl)pentyl)-N$^6$-propyl-4,5,6,7-tetrahydrobenzo[d]thiazole-2,6-diamine (33)

Aldehyde 31 (0.157 g, 0.706 mmol), (±) Pramipexole (0.15 g, 0.709 mmol), and NaBH(OAc)$_3$ (0.27 g, 1.27 mmol) in DCM (9 mL) and MeOH (0.8 mL) were reacted using procedure D' and the resulting crude was purified by column chromatography using 5-7% MeOH in DCM to give compound (0.17 g, 57%). $^1$H NMR (400 MHz, CDCl$_3$) δ ppm 6.75 (d, J=8.8 Hz, 1H), 6.70 (d, J=2.4 Hz, 1H), 6.66 (dd, J=8.8, 2.1 Hz, 1H), 3.75 (s, 3H), 3.74 (s, 3H), 3.07 (bs, 1H), 2.69 (dd, J=12.0, 4.04 Hz, 2H), 2.47-2.58 (m, 8H), 1.99-2.03 (m, 1H), 1.68-1.78 (m, 1H), 1.40-1.61 (m, 6H), 1.31-1.37 (m, 2H), 0.89 (t, J=7.2 Hz, 3H).

(R)—N$^6$-(5-(2,5-dimethoxyphenyl)pentyl)-N$^6$-propyl-4,5,6,7-tetrahydrobenzo[d]thiazole-2,6-diamine (−33)

Aldehyde 31 (0.105 g, 0.473 mmol), (−) Pramipexole (0.10 g, 0.473 mmol), and NaBH(OAc)$_3$ (0.27 g, 0.849 mmol) in DCM (7 mL) and MeOH (0.6 mL) were reacted using procedure D' and the resulting crude was purified by column chromatography using 5-7% MeOH in DCM to give compound (0.105 g, 53%). $^1$H NMR (600 MHz, CDCl$_3$) δ ppm 6.76 (d, J=8.4 Hz, 1H), 6.71 (d, J=1.8 Hz, 1H), 6.67 (dd, J=8.4, 3.0 Hz, 1H), 4.71 (bs, 2H), 3.77 (s, 3H), 3.76 (s, 3H), 3.04 (bs, 1H), 2.69 (d, J=7.2 Hz, 2H), 2.4-2.6 (m, 8H), 2.0 (bs, 1H), 1.62-1.72 (m, 2H), 1.55-1.61 (m, 2H), 1.41-1.52 (m, 3H), 1.33-1.37 (m, 2H), 0.88 (t, J=7.2 Hz, 3H).

Procedure F'. 4-(5-((2-Amino-4,5,6,7-tetrahydrobenzo[d]thiazol-6-yl)(propyl)amino)pentyl)benzene-1,2-diol (34)

BBr$_3$ 1 M in DCM (2.66 mL, 2.66 mmol) was added to a solution of compound 32 (0.2 g, 0.532 mmol) in DCM (20 mL) at −78° C. and stirred for 2 h. The reaction mixture was allowed to come to room temperature and stirred for another 4 h. The reaction was then quenched by methanol (20 mL) at 0° C. and the solvent was concentrated in vacuo, and MeOH (20 mL) was added to the residue and again evaporated. This process was repeated three times. The residue obtained was purified by column chromatography using 10-15% methanol in DCM to give pure compound 34 (123 mg, 64%). $^1$H NMR (400 MHz, CD$_3$OD) δ ppm 6.64 (d, J=8.0 Hz, 1H), 6.60 (d, J=2.4 Hz, 1H), 6.47 (dd, J=8.0, 2.4 Hz, 1H), 3.35-3.40 (m, 1H), 2.75-2.85 (m, 5H), 2.62-2.71 (m, 2H), 2.55-2.57 (m, 1H), 2.47 (t, J=7.2 Hz, 2H), 2.09-2.14 (m, 1H), 1.79-1.89 (m, 1H), 1.57-1.64 (m, 6H), 1.31-1.38 (m, 2H), 0.95 (t, J=7.6 Hz, 3H). The free base was converted into its corresponding hydrochloride salt. Mp 196-198° C. Anal. (C$_{21}$H$_{34}$N$_3$Cl$_3$O$_2$S) C, H, N.

(R)-4-(5-((2-Amino-4,5,6,7-tetrahydrobenzo[d]thiazol-6-yl)(propyl)amino)pentyl)benzene-1,2-diol (−34)

BBr$_3$ 1 M in DCM (1.61 mL, 1.61 mmol) was reacted with compound −32 (0.132 g, 0.327 mmol) in DCM (10 mL) according to Procedure F' to afford crude which was purified by column chromatography using 10-15% MeOH in DCM to give compound −11 (0.09 g, 70%). $^1$H NMR (600 MHz, CD$_3$OD) δ ppm 6.63 (d, J=7.8 Hz, 1H), 6.58 (d, J=1.8 Hz, 1H), 6.45 (dd, J=7.8, 1.8 Hz, 1H), 2.97-3.02 (m, 1H), 2.42-2.62 (m, 10H), 1.95-1.97 (m, 1H), 1.60-1.73 (m, 1H), 1.53-1.58 (quintet, J=7.8 Hz, 2H), 1.42-1.48 (septet, J=7.2

Hz, 4H), 1.26-1.31 (quintet, J=7.2 Hz, 2H), 0.88 (t, J=7.2 Hz, 3H). The free base was converted into its corresponding hydrochloride salt. Mp 211-212° C. Anal. ($C_{21}H_{35}N_3Cl_2O_2S$) C, H, N.

2-(5-((2-Amino-4,5,6,7-tetrahydrobenzo[d]thiazol-6-yl)(propyl)amino)pentyl)benzene-1,4-diol (35)

BBr$_3$ 1 M in DCM (2.27 mL, 2.27 mmol) was reacted with compound 33 (0.16 g, 0.383 mmol) according to Procedure F' to afford crude which was purified by column chromatography using 10-15% MeOH in DCM to afford compound 35 (0.12 g, 80%). $^1$H NMR (600 MHz, CD$_3$OD) δ ppm 6.55 (d, J=8.4 Hz, 1H), 6.51 (d, J=3.0 Hz, 1H), 6.41 (dd, J=8.4, 3.0 Hz, 1H), 3.0 (m, 1H), 2.44-2.63 61 (m, 10H), 1.98 (d, J=10.2 Hz, 1H), 1.65-1.68 (m, 1H), 1.56-1.61 (m, 2H), 1.44-1.52 (m, 4H), 1.32-1.36 (m, 2H), 0.88 (t, J=7.2 Hz, 3H). The free base was converted into its corresponding hydrochloride salt. Mp 217-219° C. Anal. ($C_{21}H_{35.8}N_3Cl_3O_{2.9}S$) C, H, N.

(R)-2-(5-((2-Amino-4,5,6,7-tetrahydrobenzo[d]thiazol-6-yl)(propyl)amino)pentyl)benzene-1,4-diol (−35)

BBr$_3$ 1 M in DCM (1.33 mL, 1.33 mmol) was reacted with compound (0.093 g, 0.222 mmol) in DCM (6 mL) according to Procedure F' to afford crude which was purified by column chromatography using 10-15% MeOH in DCM to give compound −35 (62 g, 72%). $^1$H NMR (600 MHz, CD$_3$OD) δ ppm 6.56 (dd, J=8.4, 1.8 Hz, 1H), 6.52 (d, J=2.4 Hz, 1H), 6.43 (dt, J=8.4, 1.80 Hz, 1H), 2.98-3.03 (m, 1H), 2.44-2.64 (m, 10H), 1.99-2.00 (m, 1H), 1.63-1.71 (m, 1H), 1.57-1.62 (m, 2H), 1.46-1.52 (m, 4H), 1.32-1.37 (m, 2H), 0.90 (t, J=7.2 Hz, 3H). The free base was converted into its corresponding hydrochloride salt. Mp 222-224° C. Anal. ($C_{21}H_{34}N_3Cl_3O_2S$) C, H, N.

Procedure G'. (Z)-ethyl 5-(4-((tert-butyldimethylsilyl)oxy)-3-methoxyphenyl)pent-4-enoate (36)

Imidazole (0.411 g, 6.03 mmol) was added to a solution of intermediate 26 (0.61 g, 2.41 mmol) and tert-butyldimethylsilyl chloride (0.437 g, 2.89 mmol) in DMF (5 mL). The solution was stirred at room temperature for 2 h. After the completion of reaction, saturated aq NaHCO$_3$ (10 mL) was added and stirred for another 30 min. The reaction mixture was extracted with DCM (2×50 mL). The combined organic layer was dried over sodium sulfate and concentrated in vacuo. The crude thus obtained was purified by column chromatography using 5% ethyl acetate in hexanes to afford compound (0.88 g) in quantitative yield. $^1$H NMR (400 MHz, CD$_3$OD) δ ppm 6.85 (s, 1H), 6.79 (d, J=8.0 Hz, 1H), 6.73 (d, J=8.4 Hz, 1H), 4.37 (d, J=11.2 Hz, 1H), 5.47-5.55 (m, 1H), 4.10 (m, J=7.2 Hz, 2H), 3.78 (s, 3H), 2.63 (q, J=7.2 Hz, 2H), 2.44 (t, J=7.2 Hz, 2H), 1.20 (t, J=7.2 Hz, 3H), 0.99 (s, 9H), 0.13 (s, 6H).

Procedure H'. (Z)-5-(4-((tert-butyldimethylsilyl)oxy)-3-methoxyphenyl)pent-4-en-1-ol (37)

Into a stirring solution of compound (0.86 g, 2.34 mmol) in anhydrous THF (15 mL) was added DIBAL-H solution 1 M in THF (11.8 mL, 11.8 mmol) dropwise at −10° C. The reaction mixture was stirred at room temperature for 6 h and was quenched with methanol (1 mL). The mixture was acidified to neural with 1N HCl (15 mL) solution. The organic layer was separated and the aqueous layer was extracted with ethyl acetate (2×100 mL). The combined organic layer was dried over sodium sulfate and concentrated in vacuo. The crude product was purified by column chromatography using 11-15% ethyl acetate in hexanes to give compound (0.63 g, 87%). $^1$H NMR (CDCl$_3$, 400 MHz) δ ppm 6.74-6.85 (m, 3H), 6.37 (d, J=11.2 Hz, 1H), 5.48-5.53 (m, 1H), 3.80 (s, 3H), 2.67 (q, J=7.2 Hz, 2H), 2.43 (t, J=7.2 Hz, 2H), 1.22 (t, J=7.2 Hz, 2H), 1.06 (s, 9H), 0.15 (s, 6H).

Procedure I'. (Z)-5-(4-((tert-butyldimethylsilyl)oxy)-3-methoxyphenyl)pent-4-enal (38)

Alcohol (0.9 g, 2.46 mmol) was slowly added to a ice cooled suspension of PCC (0.707 g, 3.28 mmol) in DCM (90 mL) and the mixture was stirred at rt for 9 h. The reaction mixture was then filtered over celite and solvent was evaporated to get residue which was purified by column chromatography using 10-15% of ethyl acetate in hexanes to give compound 15 (0.358 g, 45%). $^1$H NMR (CDCl$_3$, 400 MHz) δ ppm 9.78 (s, 1H), 6.74-6.85 (m, 3H), 6.37 (d, J=11.2 Hz, 1H), 5.49-5.52 (m, 1H), 3.80 (s, 3H), 2.56-2.68 (m, 4H), 0.99 (s, 9H), 0.16 (s, 6H).

(Z)-4-(5-((2-amino-4,5,6,7-tetrahydrobenzo[d]thiazol-6-yl)(propyl)amino)pent-1-en-1-yl)-2-methoxyphenol (39)

Compound 38 (0.315 g, 0.982 mmol) was dissolved in THF (5 mL) and cooled to 0° C. TBAF 1M in THF (1.02 mL, 1.02 mmol) was added and reaction stirred in ice for 1.5 h. After reaction was complete, 10% NaHCO3 solution (10 mL) was added and reaction mixture was extracted with DCM (3×50 mL) to obtain aldehyde which was immediately taken to the next step without further purification. Aldehyde (0.195 g, 0.945 mmol), (±) Pramipexole (0.20 g, 0.946 mmol), and NaBH(OAC)$_3$ (0.36 g, 1.69 mmol) in DCM (7 mL) and MeOH (1.0 mL) were reacted using procedure D' and the resulting crude was purified by column chromatography using 5-7% MeOH in DCM to give compound 39 (0.148 g, 39%). $^1$H NMR (400 MHz, CD$_3$OD) δ ppm 6.86 (d, J=8.0 Hz, 1H), 6.76-6.82 (m, 2H), 6.35 (d, J=12.4 Hz, 1H), 5.49-5.56 (m, 1H), 4.98 (bs, 1H), 3.86 (s, 3H), 3.1 (bs, 1H), 2.50-2.71 (m, 8H), 2.37 (q, J=7.2 Hz, 2H), 2.03 (bs, 1H), 1.44-1.70 (m, 5H), 0.88 (t, J=7.2 Hz, 3H). The free base was converted into its corresponding hydrochloride salt. Mp 212-214° C. Anal. ($C_{22}H_{34.4}N_3Cl_3O_{2.2}S$) C, H, N.

Figure 15:
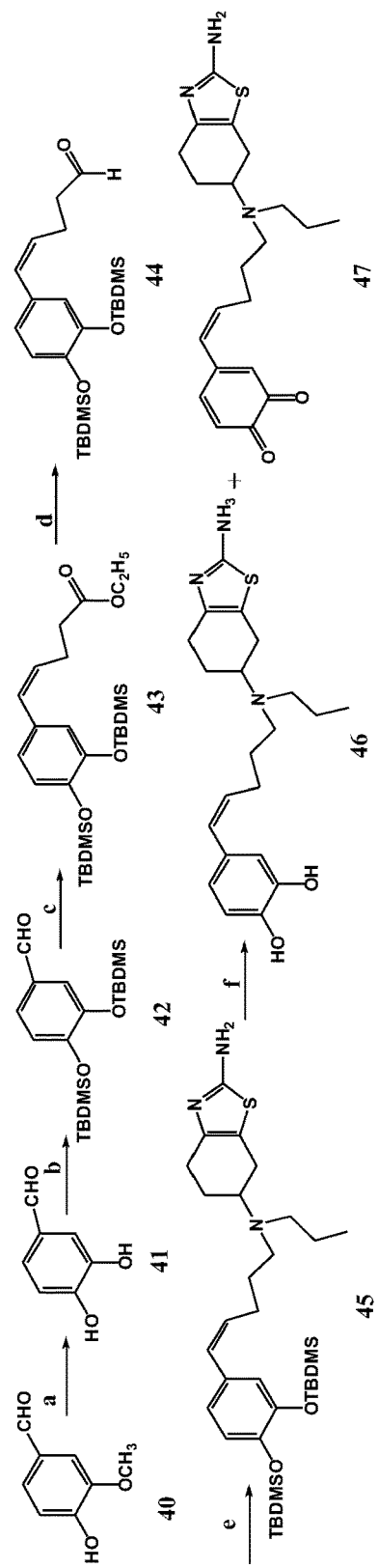
FIG. 15 provides a synthetic scheme for compounds having formula II.

FIG. 15 provides a synthetic scheme for the compounds having formula II, specifically for compound 47. The reaction conditions for this scheme are: (a) BBr$_3$, DCM, −78° C. to rt, 6 h, 87%; (b) TBDMSCl, imidazole, DMF, rt, 2 h, 67%; (c) Phosphonium bromide 2, THF, −78° C. to rt, 48 h; 39%; (d) DIBALH, toluene, −78° C., 2 h, 45%; (e) Pramipexole, NaBH(OAc)$_3$, DCM, rt, 36 h, 50%; (0 TBAF, THF, 0° C., 1.5 h, 72%.

3,4-dihydroxybenzaldehyde (41)

Vanillin 40 (3.0 g, 18.0 mmol) was reacted with BBr$_3$ 1 M in DCM (36.1 mL, 36.1 mmol) in DCM (20 mL) following Procedure F'. The crude obtained was purified by column chromatography using 20-25% ethyl acetate in hexanes to afford compound 41 (2.18 g, 87%). $^1$H NMR (400 MHz, CDCl$_3$) δ ppm 9.67 (s, 1H, CHO), 7.29 (m, 2H), 6.89 (d, J=9.2 Hz, 1H).

3,4-bis((tert-butyldimethylsilyl)oxy)benzaldehyde (42)

Imidazole (5.69 g, 83.5 mmol) was added to a solution of intermediate 41 (2.31 g, 16.7 mmol) and tert-butyldimethylsilyl chloride (6.30 g, 41.8 mmol) in DMF (20 mL). The solution was reacted using Procedure G'. The crude thus obtained was purified by column chromatography using 5% ethyl acetate in hexanes to afford compound 42 (4.10 g, 67%). $^1$H NMR (400 MHz, CDCl$_3$) δ ppm 9.80 (s, 1H, CHO), 7.36 (m, 2H), 6.93 (d, J=8.8 Hz, 1H), 0.99 (s, 9H), 0.98 (s, 9H), 0.24 (s, 6H), 0.22 (s, 6H).

(Z)-ethyl 5-(3,4-bis((tert-butyldimethylsilyl)oxyphenyl)pent-4-enoate (43)

Starting material 25 (5.48 g, 11.98 mmol) was reacted with compound 42 (4.0 g, 10.90 mmol) in presence of NaHMDS 1M in THF (13.07 mmol, 13.07 mL) according to Procedure A'. The crude was purified by column chromatography using 5% ethyl acetate in hexanes to give compound 20 (2.0 g, 39%). $^1$H NMR (400 MHz, CDCl$_3$) δ ppm 6.81 (m, 2H), 6.73 (d, J=8.4 Hz, 1H), 6.30 (d, J=11.4 Hz, 1H), 5.46-5.50 (m, 1H), 4.12 (q, J=7.3 Hz, 2H), 2.64 (q, J=7.2 Hz, 2H), 2.41 (t, J=7.2 Hz, 2H), 1.24 (t, J=7.2 Hz, 3H), 0.97 (s, 18H), 0.19 (s, 6H), 0.18 (s, 6H).

(Z)-ethyl 5-(3,4-bis((tert-butyldimethylsilyl)oxyphenyl)pent-4-enal (44)

Intermediate 43 (1.0 g, 2.15 mmol) was reduced with DIBALH solution 1M in hexane (2.16 mL, 2.16 mmol) in dry toluene (15 mL) using procedure D'. The crude was purified by column chromatography using 10% ethyl acetate in hexane to give compound 44 (0.41 gm, 45%) as yellow oil. $^1$H NMR (600 MHz, CDCl$_3$) δ ppm 9.76 (s, 1H), 6.77-6.79 (m, 2H), 6.73 (td, J=7.2, 2.4 Hz, 1H), 6.33 (d, J=11.4 Hz, 1H), 5.45-5.50 (m, 1H), 2.65 (q, J=7.2 Hz, 2H), 2.56 (t, J=7.2 Hz, 2H), 0.98 (s, 18H), 0.20 (s, 12H).

(Z)—N$^6$-(5-(3,4-bis((tert-butyldimethylsilyl)oxy)phenyl)pent-4-en-1-yl)-N$^6$-propyl-4,5,6,7-tetrahydrobenzo[d]thiazole-2,6-diamine (45)

Aldehyde 44 (0.3 g, 0.71 mmol), (±) Pramipexole (0.15 g, 0.71 mmol), and NaBH(OAc)$_3$ (0.27 g, 1.27 mmol) in DCM (10 mL) and MeOH (0.8 mL) were reacted using procedure E' and the resulting crude was purified by column chromatography using 5% MeOH in DCM to give compound 45 (0.22 g, 50%). $^1$H NMR (600 MHz, CD$_3$OD) δ ppm 6.79 (m, 2H), 6.73 (d, J=7.8 Hz, 1H), 6.29 (d, J=11.4 Hz, 1H), 5.52 (m, 1H), 3.09 (bs, 1H), 2.44-2.66 (m, 8H), 2.34-2.37 (m, 2H), 1.96-1.99 (m, 1H), 1.60-1.72 (m, 3H), 1.44-1.51 (m, 2H), 0.97 (s, 18H), 0.87 (t, J=7.2 Hz, 3H), 0.18 (s, 12H).

Procedure J'. (Z)-4-(5-((2-amino-4,5,6,7-tetrahydrobenzo[d]thiazol-6-yl)(propyl)amino)pent-1-en-1-yl)benzene-1,2-diol and 4-(5-((2-amino-4,5,6,7-tetrahydrobenzo[d]thiazol-6-yl)(propyl)amino)pent-1-enyl)-[1,2]benzoquinone (mixture of 46 and 47)

Compound (0.21 g, 0.34 mmol) was dissolved in THF (5 mL) and cooled to 0° C. TBAF 1M in THF (1.02 mL, 1.02 mmol) was added and reaction stirred in ice for 1.5 h. After reaction was complete, 10% NaHCO$_3$ solution (10 mL) was added and reaction mixture was extracted with DCM (3×50 mL). The combined organic layer was dried over sodium sulfate and concentrated in vacuo. The crude was purified by column chromatography using 15-20% MeOH in DCM (0.095 g, 72%). $^1$H NMR (600 MHz, CD$_3$OD) δ ppm 6.79 (s, 1H), 6.73 (s, 1H), 6.70 (d, J=7.8 Hz, 1H), 6.63 (m, 2H), 6.59 (d, J=8.4 Hz, 1H), 6.20-6.25 (m, 2H), 6.59 (dt, J=15.6, 7.2 Hz, 1H), 5.46 (m, 1H), 3.0 (bs, 2H), 2.40-2.63 (m, 16H), 2.32 (m, 2H), 2.16 (m, 2H), 1.95 (m, 2H), 1.56-1.70 (m, 6H), 1.41-1.51 (m, 4H), 0.85-0.90 (m, 6H). The free base was converted into its corresponding hydrochloride salt. Mp 212-214° C. Anal. (C$_{22}$H$_{34.4}$N$_3$Cl$_3$O$_{2.2}$S) C, H, N.

Figure 16:
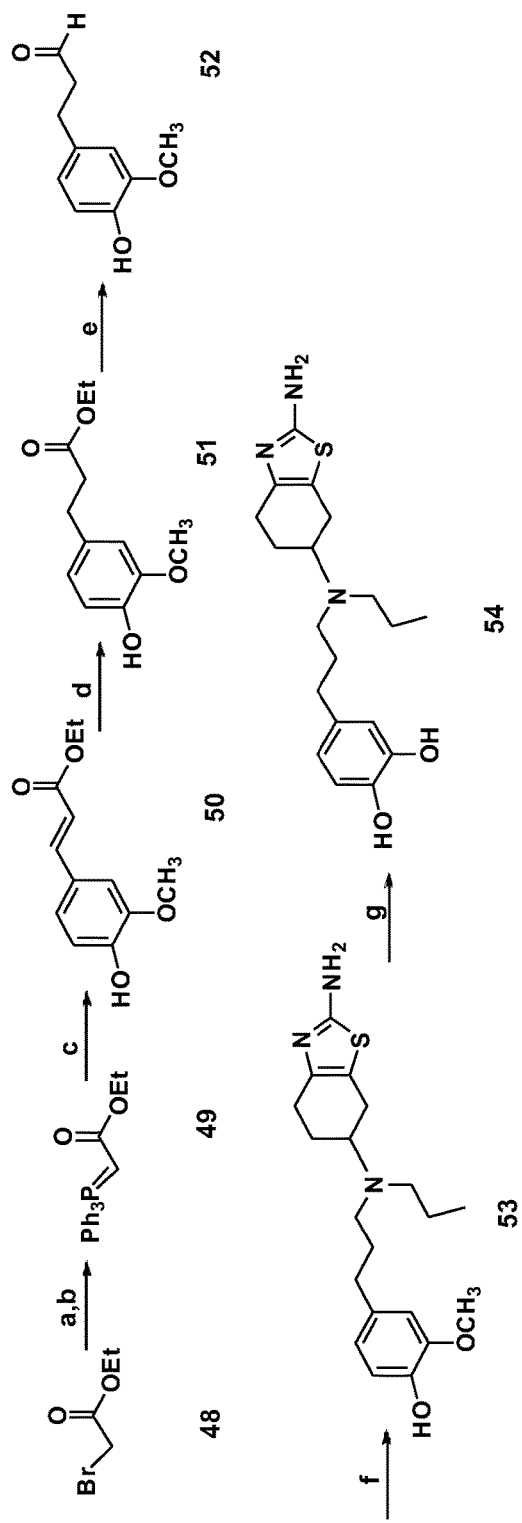
FIG. 16 provides a synthetic scheme for compounds having formula II.

FIG. 16 provides a synthetic scheme for the compounds having formula II, specifically for compound 54. The reaction conditions for this scheme are: (a) TPP, toluene, reflux, 16 h, 87%; (b) 1 M NaOH aq., 15 min, 88%; (c) Vanillin, DCM, reflux, 5 h, 85% (d) 10% pd/C, H$_2$, ethanol, rt, 2 h, quant. yield; (d) DIBALH, toluene, −78° C., 2 h, 45%; (e) Pramipexole, NaBH(OAc)$_3$, DCM, rt, 36 h, 46%; (f) BBr$_3$, DCM 0° C.-rt, 6 h, 63%.

(ethyl 2-(triphenylphosphoranylidene)acetate (49)

Ethyl bromoacetate (1.98 mL, 17.90 mmol) was slowly added to a stirring solution of triphenylphosphine (5.64 g, 21.50 mmol) in toluene (20 mL). The reaction mixture was refluxed for 16 h and filtered. The filter cake was washed with ethyl acetate (3×20 mL) to give phosphonium bromide (6.69 g, 87%). Into a solution of phosphonium bromide (6 g, 13.98 mmol) in DCM (50 mL) was added an aqueous solution of NaOH (1.0 M, 50 mL). The mixture was vigorously stirred for 15 min and the layers were separated. The aqueous layer was extracted with DCM (3×15 mL). The combined organic phase was dried over Na$_2$SO$_4$ and concentrated to give compound 49 (4.28 g, 88%). $^1$H NMR (CDCl$_3$, 400 MHz): δ (0.65, minor+1.21, major) (t, J=7.2 Hz, 3H), (2.70, minor+2.92, major) (d, J=22 Hz, 1H), (3.80, minor+4.01, major) (q, J=7.2 Hz, 2H), 7.40-7.77 (m, 15H).

Ethyl 3-(4-hydroxy-3-methoxyphenyl)acrylate (50)

Intermediate 49 (3.10 g, 7.23 mmol) was reacted with NaHMDS (1M in THF, 7.88 mL, 7.88 mmol) and Vanillin (1.0 g, 6.57 mmol) in anhydrous THF (8 mL) according to Procedure B' The crude thus obtained was purified by column chromatography using 7-10% ethyl acetate in hexanes to yield compound 50 (1.25 g, 85%) as colorless oil with a preferential Z:E ratio of >20:1: $^1$H NMR (400 MHz, CDCl$_3$,) δ ppm 7.03 (m, ArH, 2H), 6.91 (d, J=8.0 Hz, ArH, 1H), 6.29 (d, J=15.2 Hz, 1H), 5.83 (m, 1H), 4.25 (q, J=7.2 Hz, OCH$_2$, 2H), 3.92 (s, OCH$_3$, 3H), 1.33 (t, J=7.6 Hz, 3H).

Ethyl 3-(4-hydroxy-3-methoxyphenyl)propanoate (51)

Intermediate 50 (1.0 g, 4.45 mmol) was dissolved in ethanol (10 mL) in a round bottom flask and 10% Pd/C (0.10 g, 10 wt %) was added to it. The reaction was continued using Procedure C'. After the completion of reaction, the mixture was diluted with ethanol (20 mL) and passed through a short bed of celite. The organic layer was concentrated to afford compound 51 (0.95 gm) as colorless oil in quantitative yield which was pure enough for the next step. $^1$H NMR (400 MHz, CDCl$_3$) δ ppm 6.82 (d, J=7.2 Hz, 1H), 6.68 (m, 2H), 4.12 (q, J=7.2 Hz, 2H), 3.84 (s, 3H), 2.87 (t, J=7.6 Hz, 2H), 2.58 (t, J=8.0 Hz, 2H), 1.23 (t, J=7.2 Hz, 3H).

3-(4-Hydroxy-3-methoxyphenyl)propanal (52)

Intermediate 51 (0.60 g, 2.67 mmol) was reduced with DIBALH solution (1M in hexane, 2.93 mL, 2.93 mmol) in dry toluene (10 mL) using procedure D'. The crude was purified by column chromatography using 12-15% ethyl acetate in hexanes to give compound 52 (0.22 gm, 45%) as yellow oil. $^1$H NMR (400 MHz, CDCl$_3$) δ ppm 9.81 (t, J=1.6 Hz, 1H), 6.83 (d, J=7.2 Hz, 1H), 6.68 (m, 2H), 3.87 (s, 3H), 2.89 (t, J=7.6 Hz, 2H), 2.75 (t, J=8.0 Hz, 2H).

4-(3-((2-Amino-4,5,6,7-tetrahydrobenzo[d]thiazol-6-yl)(propyl)amino)propyl)-2-methoxyphenol (53)

Aldehyde 52 (0.30 g, 1.66 mmol), (±) Pramipexole (0.369 g, 1.74 mmol), and NaBH(OAc)$_3$ (0.633 g, 2.98 mmol) in DCM (10 mL) and MeOH (1 mL) were reacted using procedure E' and the resulting crude was purified by column chromatography using 5-7% MeOH in DCM to give compound 53 (0.2 g, 46%). $^1$H NMR (400 MHz, CD$_3$OD) δ ppm 6.79 (s, 1H), 6.71 (d, J=8.0 Hz, 1H), 6.64 (d, J=8.0 Hz, 1H), 3.82 (s, 3H), 2.73-2.89 (m, 5H), 2.57-2.67 (m, 6H), 2.05-2.12 (m, 1H), 1.81-1.92 (m, 3H), 1.59 (m, 2H), 0.95 (t, J=7.2 Hz, 3H). The free base was converted into its corresponding hydrochloride salt. Mp 220-222° C. Anal. (C$_{20}$H$_{32}$Cl$_2$N$_3$O$_{2.5}$S) C, H, N.

4-(3-((2-Amino-4,5,6,7-tetrahydrobenzo[d]thiazol-6-yl)(propyl)amino)propyl)-benzene-1,4-diol (54)

BBr$_3$ 1 M in DCM (2.66 mL, 2.66 mmol) was reacted with compound 53 (0.2 g, 0.532 mmol) according to Procedure F' to afford crude which was purified by column chromatography using 15-20% MeOH in DCM to provide compound 54 (0.12 g, 63%) $^1$H NMR (400 MHz, CD$_3$OD) δ ppm 6.57 (d, J=8.4 Hz, 1H), 6.53 (s, 1H), 6.41 (d, J=8.4 Hz, 1H), 3.13 (bs, 1H), 2.39-2.66 (m, 10H), 1.95 (m, 1H), 1.61-1.75 (m, 3H), 1.41-1.47 (m, 2H), 0.82 (t, J=7.2 Hz, 3H). The free base was converted into its corresponding hydrochloride salt. Mp 192-194° C. Anal. (C$_{19}$H$_{30.6}$N$_3$Cl$_3$O$_{2.3}$S) C, H, N.

Elemental Analysis Report of Final Compounds (2-ethoxy-2-oxoethyl)triphenylphosphonium bromide (56)

Ethyl bromoacetate (1.98 mL, 17.90 mmol) was slowly added to a stirring solution of triphenylphosphine (5.64 g, 21.50 mmol) in toluene (20 mL). The reaction mixture was refluxed for 16 h and filtered. The filter cake was washed with ethyl acetate (3×20 mL) to give compound 2 (6.69 g, 87%). $^1$H NMR (CDCl$_3$, 400 MHz): δ 1.04 (t, J=7.2 Hz, 3H), 4.01 (q, J=7.2 Hz, 2H), 5.54 (d, J=13.6 Hz, 2H), 7.64-7.91 (m, 15H).

ethyl 2-(triphenylphosphoranylidene)acetate (57)

Into a solution of phosphonium bromide 54 (6 g, 13.98 mmol) in DCM (50 mL) was added an aqueous solution of NaOH (1.0 M, 50 mL). The mixture was vigorously stirred for 15 min and the layers were separated. The aqueous layer was extracted with DCM (3×15 mL). The combined organic phase was dried over Na$_2$SO$_4$ and concentrated to give compound 57 (4.28 g, 88%). $^1$H NMR (CDCl$_3$, 400 MHz): δ (0.65, minor+1.21, major) (t, J=7.2 Hz, 3H), (2.70, minor+2.92, major) (d, J=22 Hz, 1H), (3.80, minor+4.01, major) (q, J=7.2 Hz, 2H), 7.40-7.77 (m, 15H).

(E)-ethyl 3-(4-hydroxy-3-methoxyphenyl)acrylate (58)

A mixture of vanillin (1.65 g, 10.84 mmol) and phosphonium ylide 57 (4.08 g, 11.71 mmol) was refluxed in chloroform (30 mL) for 5 h. The solvent was removed and the crude product was purified by column chromatography (17% ethyl acetate in Hexane) to give compound 58 (2.05 g, 85%). $^1$H NMR (CDCl$_3$, 400 MHz): δ 1.19 (t, J=7.2 Hz, 3H), 3.70 (s, 3H), 4.13 (q, J=7.0 Hz, 2H), 6.17 (d, J=15.7 Hz, 1H), 6.75-6.92 (m, 3H), 7.49 (d, J=15.9 Hz, 1H).

|  | Calculated | | | Found | | |
|---|---|---|---|---|---|---|
| Compound | C | H | N | C | H | N |
| (9). 2HCl•0.58C$_2$H$_5$OH•0.22CH$_3$SOCH$_3$ (D-548) | 4.47 | 7.71 | 8.07 | 4.86 | 7.31 | 7.60 |
| (−9). 2HCl•H$_2$O | 53.43 | 7.34 | 8.75 | 51.97 | 7.25 | 4.41 |
| (11). 3HCl (D-575) | 50.55 | 6.87 | 8.42 | 50.33 | 7.01 | 8.53 |
| (−11). 2HCl•H$_2$O | 52.49 | 7.34 | 8.75 | 51.97 | 7.25 | 8.41 |
| (12). 3HCl•0.9H$_2$O (D-584) | 48.96 | 7.00 | 8.16 | 49.35 | 6.76 | 7.75 |
| (−12). 3HCl (D-601) | 50.55 | 6.87 | 8.42 | 50.26 | 7.14 | 8.23 |
| (16). 3HCl•0.2H$_2$O (D-567) | 51.35 | 6.74 | 8.17 | 51.65 | 7.16 | 7.63 |
| (23). 3HCl | 50.76 | 6.49 | 8.46 | 50.07 | 7.33 | 7.97 |
| (30). 2HCl•0.5H$_2$O (D-547) | 52.51 | 7.05 | 9.19 | 52.12 | 7.19 | 8.83 |
| (31). 3HCl•0.3H2O (D-573) | 47.91 | 6.48 | 8.82 | 47.86 | 6.87 | 9.23 |

Figure 17:
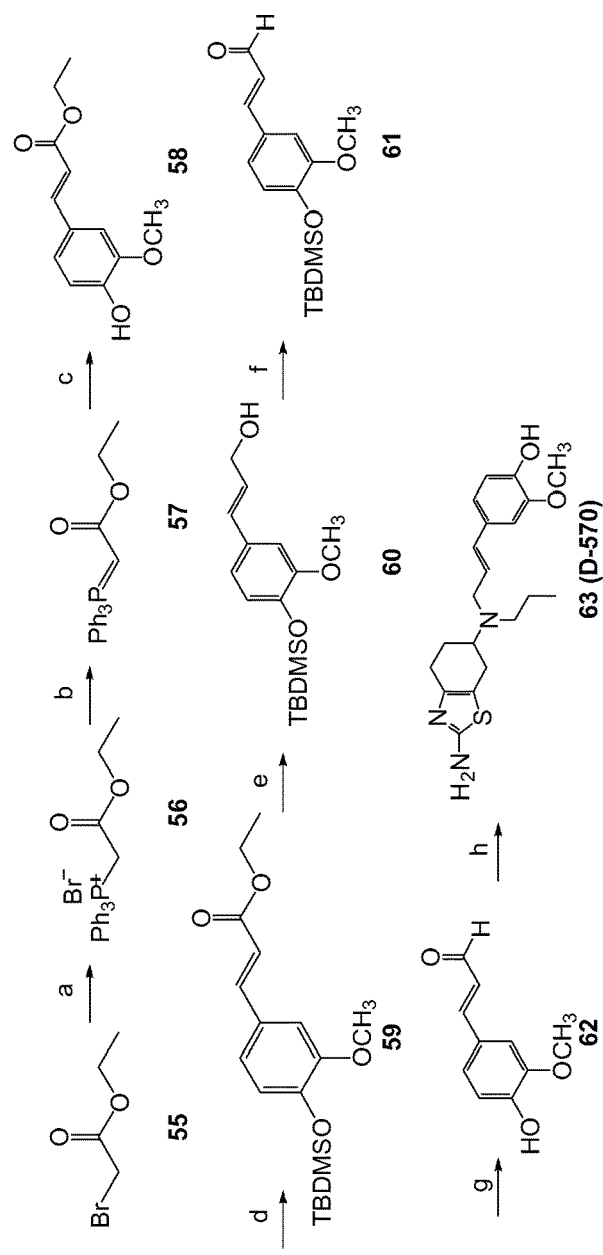
FIG. 17 provides a synthetic scheme for compounds having formula II.

FIG. 17 provides a synthetic scheme for the compounds having formula II, specifically for compound 63. The conditions for this scheme are: (a) TPP, toluene, reflux, 16 h, 87%; (b) 1 M NaOH aq., 15 min, 88%; (c) vanillin, CHCl$_3$, reflux, 5 h, 85%; (d) TBDMSCl, imidazole, DMF, rt, 2 h, 90%; (e) DIBALH, THF, −10° C. to rt, 6 h, 94%; (f) MnO$_2$, DCM, rt, 24 h, 84%; (g) TBAF, THF, 0° C., 1 h, 84%; (h) (±) Pramipexole, NaBH(OAc)$_3$, DCM, rt, 48 h, 30%.

(E)-ethyl 3-(4-((tert-butyldimethylsilyl)oxy)-3-methoxyphenyl)acrylate (59)

A solution of compound 58 (1.78 g, 8.01 mmol), tert-butyldimethylsilyl chloride (1.45 g, 9.62 mmol), and Imidazole (1.36 g, 19.98 mmol) in DMF (6 mL) was stirred at room temperature for 2 h. Then the mixture was extracted with water and diethyl ether. The organic phase was washed with brine and dried over Na$_2$SO$_4$. Then it was concentrated to give compound 5 (2.42 g, 90%). $^1$H NMR (CDCl$_3$, 400 MHz): δ 0.17 (s, 6H), 0.99 (s, 9H), 1.33 (t, J=7.2 Hz, 3H), 3.83 (s, 3H), 4.25 (q, J=7.1 Hz, 2H), 6.30 (d, J=16.0 Hz, 1H), 6.84 (d, J=8.8 Hz, 1H), 6.99-7.03 (m, 2H), 7.62 (d, J=15.2 Hz, 1H).

(E)-3-(4-((tert-butyldimethylsilyl)oxy)-3-methoxyphenyl)prop-2-en-1-ol (60)

Into a stirring solution of compound 59 (2.4 g, 7.13 mmol) in anhydrous THF (30 mL) was added DIBAL-H solution (1 M in THF, 35.7 mL, 35.7 mmol) dropwise at −10° C. The reaction mixture was stirred at room temperature for 6 h and was quenched with methanol (1 mL). The mixture was acidified to neural with 1N HCl solution. The organic layer was separated and the aqueous layer was extracted with ethyl acetate (2×20 mL). The combined organic phase was dried over Na$_2$SO$_4$ and concentrated. The crude product was purified by column chromatography (25% ethyl acetate in Hexane) to give compound 60 (1.97 g, 94%). $^1$H NMR (CDCl$_3$, 400 MHz): δ 0.15 (s, 6H), 0.99 (s, 9H), 3.81 (s, 3H), 4.28 (d, J=5.6 Hz, 2H), 6.22 (dt, J=16.0, 6.0 Hz, 1H), 6.52 (d, J=15.6 Hz, 1H), 6.79 (d, J=8.0 Hz, 1H), 6.84 (dd, J=8.0, 1.6 Hz, 1H), 6.90 (d, J=1.6 Hz, 1H).

(E)-3-(4-((tert-butyldimethylsilyl)oxy)-3-methoxyphenyl)acrylaldehyde (61)

MnO$_2$ (3.54 g, 40.72 mmol) was added into a solution of compound 60 (0.8 g, 2.72 mmol) in DCM (15 mL). The mixture was stirred at room temperature for 24 h and was filtered through celite. The filter cake was washed with ethyl acetate and the filtrate was concentrated to give compound 61 (0.67 g, 84%). $^1$H NMR (CDCl$_3$, 400 MHz): δ 0.18 (s, 6H), 1.00 (s, 9H), 3.85 (s, 3H), 6.60 (dd, J=15.6, 7.6 Hz, 1H), 6.88 (d, J=7.2 Hz, 1H), 7.05-7.08 (m, 2H), 7.40 (d, J=16.0 Hz, 1H), 9.65 (d, J=7.2 Hz, 1H).

(E)-3-(4-hydroxy-3-methoxyphenyl)acrylaldehyde (62)

Into a stirring solution of compound 7 (0.67 g, 2.29 mmol) in THF (10 mL) at 0° C., TBAF solution (1 M in THF, 2.52 mL, 2.52 mmol) was added dropwise. The mixture was stirred for 1 h and was quenched with a saturated solution of NaHCO$_3$ (stirred for 30 min). The organic layer was separated and the aqueous layer was extracted with DCM (3×15 mL). The organic layer was dried over Na$_2$SO$_4$ and concentrated. The crude product was purified by column chromatography (35% ethyl acetate in Hexane) to give compound 62 (0.343 g, 84%). It was immediately taken to the next step.

(E)-4-(3-((2-amino-4,5,6,7-tetrahydrobenzo[d]thiazol-6-yl)(propyl)amino)prop-1-en-1-yl)-2-methoxyphenol (63)

A mixture of aldehyde 62 (0.334 g, 1.87 mmol) and (±) pramipexole (0.395 g, 1.87 mmol) in DCM (10 mL) was stirred for 1 h, and followed by the portionwise addition of NaBH(OAc)$_3$ (0.710 g, 3.35 mmol). Then the mixture was kept for stirring for 48 h at room temperature and was quenched with a saturated solution of NaHCO$_3$ afterwards at 0° C. The organic layer was separated and the aqueous layer was extracted with ethyl acetate (3×10 mL). The combined organic phase was dried over Na$_2$SO$_4$. The concentrated crude product was purified by column chromatography (15% methanol in DCM) to give compound 63 (0.21 g, 30%). $^1$H NMR (CD$_3$OD, 400 MHz): δ 1.03 (t, J=7.2 Hz, 3H), 1.72 (q, J=7.1 Hz, 2H), 1.81-2.00 (m, 2H), 2.23-2.33 (m, 1H), 2.58-2.67 (m, 1H), 2.79-2.90 (m, 3H), 2.99 (t, J=7.1 Hz, 2H), 3.25 (dd, J=15.6, 5.2 Hz, 1H), 3.46 (s, 1H), 3.89 (s, 3H), 6.81 (d, J=8.4 Hz, 1H), 6.92 (dd, J=15.2, 7.6 Hz, 1H), 7.10 (d, J=8.0 Hz, 1H), 7.20 (s, 1H), 7.36 (d, J=16.4 Hz, 1H). The free base was converted into its corresponding hydrochloride salt. Mp 205-207° C. Anal. (C$_{20}$H$_{32}$Cl$_3$N$_3$O$_3$S) C, H, N.

| | Calculated | | | Found | | |
|---|---|---|---|---|---|---|
| Compound | C | H | N | C | H | N |
| 9. 3HCl•1H$_2$O | 47.96 | 6.44 | 8.39 | 48.24 | 6.35 | 8.29 |

Figure 18:
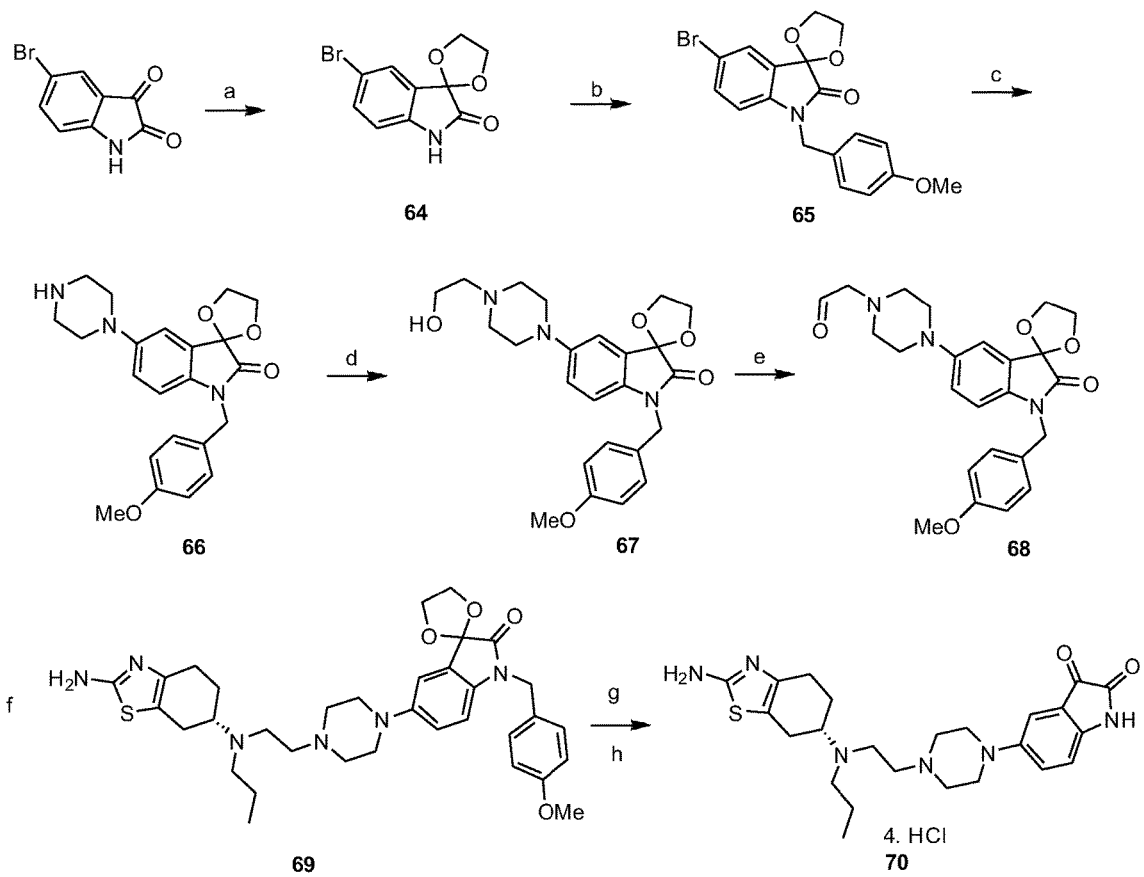
FIG. 18 provides a synthetic scheme for compounds having formula I

FIG. 18 provides a synthetic scheme for the compounds having formula I, specifically for compound 70.

Reagent and condition: (a) Ethylene glycol, Toluene, PTSA, reflux, 12 h; (b) 4-Methoxybenzylbromide, K$_2$CO$_3$, DMF, TBAI, rt, 12 h; (c) Piperazine, Pd(OAc)$_2$, BINAP, Cs$_2$CO$_3$, Toluene, reflux; (d) Bromoethanol, K$_2$CO$_3$, CH$_3$CN, reflux, 12 h; (e) (COCl)$_2$, DMSO, Et$_3$N, CH$_2$Cl$_2$, −78° C. to rt; (f) (±) (−) Pramipexole, Na(OAc)$_3$BH, CH$_2$Cl$_2$, 48 h; (g) 1:1 Conc. HCl, MeOH, sealed tube reflux, 12 h; (h) 2M HCl in ether, CH$_2$Cl$_2$.

5'-bromospiro[[1,3]dioxolane-2,3'-indolin]-2'-one (64)

To a solution of 5-bromoisatin (1 g, 4.42 mmol) in toluene (40 mL), ethylene glycol (4.9 mL, 84.48 mmol) and p-toluenesulphonic acid (38.1 mg, 0.22 mmol) were added. The reaction mixture was refluxed for 5 h and then evaporated to dryness. The residue was diluted with dichlormethane and washed with saturated sodium bicarbonate solution. The aqueous layer was extracted with dichloromethane three times. The combined organic extracts were dried over anhydrous sodium sulfate, filtered, and evaporated. The crude mixture was purified using column chromatography to yield 64. Yield: 99%. (C. H. Wang, A. R. White, S. N. Schwartz, S. Alluri, T. M. Cattabiani, L. K. Zhang, T. M. Chan, A. V. Buevich, A. K. Ganguly *Tetrahedron* 2012, 68, 9750-9762.)

5'-bromo-1'-(4-methoxybenzyl)spiro[[1,3]dioxolane-2,3'-indolin]-2'-one (65)

A mixture of compound 55 (1.75 g, 6.38 mmol), (4-Methoxybenzylbromide) (1.3 mL, 9.5 mmol), pinch of tetrabutylammonium iodide and K$_2$CO$_3$ (2.64 g g, 19.1 mmol) in DMF (15 mL) was stirred for 12 h. Quench the reaction mixture with ice cold water and extract with ethylacetate, dried over sodium sulfate and evaporated the crude material was purified by silica gel column chromatography (EtOAc/hexane, 3:1) to give compound 65 (2.25 g, 90%) $^1$H NMR (400 MHz, CDCl$_3$): δ 7.47 (d, J=1.6 Hz, 1H), 7.35 (dd, J$_1$=8.4 Hz, J$_2$=1.6 Hz, 1H), 7.18 (d, J=8.8 Hz, 2H), 7.35 (dd, J$_1$=8.4 Hz, J$_2$=1.6 Hz, 1H), 6.54 (d, J=8.0 Hz, 1H), 4.74 (s, 2H), 4.62-4.59 (m, 2H), 4.35-4.32 (m, 2H), 3.77 (s, 3H); $^{13}$C NMR (100 MHz, CDCl$_3$): δ 172.8, 159.2, 142.8, 134.2, 128.5 (2C), 128.1, 126.7, 115.8, 114.3 (2C), 111.2, 66.0, 55.2, 43.0.

1'-(4-methoxybenzyl)-5'-(piperazin-1-yl)spiro[[1,3]dioxolane-2,3'-indolin]-2'-one (66)

A mixture of 2 (1.2 g, 3.0 mmol), Piperazine (0.78 g, 9.1 mmol), Pd(OAc)$_2$ (0.034 g, 0.15 mmol), BINAP (0.142 g, 0.22 mmol) and Cs$_2$CO$_3$ (2.96 g, 9.2 mmol) in toluene (12 mL) was heated at 110° C. for 12 h. The reaction mixture was filtered through Celite, wash with dichloromethane and concentrated in vacuo. The crude residue was dissolved in ethylacetate and washed with water and evaporated to afford compound 66 (0.755 g, 62%). The crude residue was used for next step without purification. $^1$H NMR (400 MHz, CDCl$_3$): δ 7.19 (d, J=8.4 Hz, 2H), 7.01 (d, J=2.4 Hz, 1H), 6.81 (d, J=8.4 Hz, 2H), 6.77 (dd, J$_1$=8 Hz, J$_2$=2.4 Hz, 1H), 6.55 (d, J=8.8 Hz, 1H), 4.70 (s, 2H), 4.63-4.60 (m, 2H), 4.33-4.30 (m, 2H), 3.75 (s, 3H), 3.01 (d, J=5.6 Hz, 8H); $^{13}$C NMR (100 MHz, CDCl$_3$): δ 173.2, 159.0, 148.7, 136.8, 128.5 (2C), 127.4, 124.6, 119.4, 114.5 (2C), 110.1, 102.5, 65.8, 55.2, 51.1 (2C), 45.8 (2C), 42.9.

5'-(4-(2-hydroxyethyl)piperazin-1-yl)-1'-(4-methoxybenzyl)spiro[[1,3]dioxolane-2,3'-indolin]-2'-one (67)

A mixture of compound 57 (0.74 g, 1.86 mmol), (2-bromoethanol (0.26 mL, 3.7 mmol), and K$_2$CO$_3$ (0.76 g, 5.55 mmol) in CH$_3$CN (15 mL) was refluxed for 12 h. After filtration, acetonitrile was evaporated under reduced pressure and the crude material was purified by silica gel column chromatography (EtOAc/hexane, 3:1) to give compound 67 (0.631 g, 77%). $^1$H NMR (400 MHz, CDCl$_3$): δ 7.19 (d, J=9.2 Hz, 2H), 7.01 (d, J=2.4 Hz, 1H), 6.82 (d, J=9.2 Hz, 2H), 6.77 (dd, J$_1$=8 Hz, J$_2$=2.4 Hz, 1H), 6.56 (d, J=8 Hz, 1H), 4.71 (s, 2H), 4.63-4.60 (m, 2H), 4.34-4.31 (m, 2H), 3.75 (s, 3H), 3.76 (t, J=5.6 Hz, 2H), 3.53 (bs, 1H), 3.11 (t, J=4.8 Hz, 4H), 2.69 (t, J=4.8 Hz, 4H), 2.62 (t, J=5.6 Hz, 2H); $^{13}$C NMR (100 MHz, CDCl$_3$): δ 173.2, 159.0, 148.0, 136.9, 128.5 (2C), 127.3, 124.7, 119.3, 114.5, 114.1 (2C), 110.2, 102.5, 65.8 (2C), 59.3, 57.6, 55.2, 52.8 (2C), 49.9 (2C), 42.9.

2-(4-(1'-(4-methoxybenzyl)-2'-oxospiro[[1,3]dioxolane-2,3'-indolin]-5'-yl)piperazin-1-yl)acetaldehyde (68)

Into a stirring solution of oxalyl chloride (0.094 mL, 1.1 mmol) in CH$_2$Cl$_2$ (7 mL) at −78° C. was added DMSO (0.141 mL, 1.99 mmol). The reaction mixture was stirred for 0.5 h, followed by addition of compound 67 (0.25 g, 0.55 mmol, in 5 mL of CH$_2$Cl$_2$. The reaction mixture was stirred at the same temperature for 0.5 h, followed by addition of Et$_3$N (0.615 mL, 4.4 mmol), and stirring was continued for 1.5 h while allowing the reaction mixture to reach room temperature. The reaction mixture was quenched by addition of a saturated solution of NaHCO$_3$ and extracted with CH$_2$Cl$_2$ (3×100 mL). The combined organic layer was dried using Na$_2$SO$_4$, and the solvent was removed under reduced pressure. The crude product was purified by silica gel column chromatography (EtOAc/MeOH, 20:1) to give compound 68 (0.24 g, 99%). $^1$H NMR (600 MHz, CDCl$_3$): δ 9.71 (d, J=1.2 Hz, 1H), 7.19 (d, J=9.0 Hz, 2H), 7.01 (d, J=2.4 Hz, 1H), 6.81 (dd, J$_1$=6.6 Hz, J$_2$=1.8 Hz, 2H), 6.77 (dd, J$_1$=8.4 Hz, J$_2$=2.4 Hz, 1H), 6.55 (d, J=8.4 Hz, 1H), 4.71 (s, 2H), 4.63-4.61 (m, 2H), 4.33-4.31 (m, 2H), 3.75 (s, 3H), 3.22 (d, J=1.2 Hz, 2H), 3.13 (t, J=4.8 Hz, 4H), 2.65 (t, J=4.8 Hz, 4H).

5'-(4-(2-((2-amino-4,5,6,7-tetrahydrobenzo[d]thiazol-6-yl)(propyl)amino)ethyl piperazin-1-yl)-1'-(4-methoxybenzyl)spiro[[1,3]dioxolane-2,3'-indolin]-2'-one (69)

Into a stirring solution of Pramipexole (0.112 g, 5.3 mmol) in CH$_2$Cl$_2$ (50 mL) was added aldehyde 68 (0.24 g, 5.3 mmol). After the mixture was stirred for 1 h, NaBH(OAc)$_3$ (0.23 g, 1.1 mmol) was added portion wise and the mixture was stirred for 48 h at room temperature. The reaction mixture was quenched with a saturated solution of NaHCO$_3$ at 0° C. and extracted with dichloromethane (3×100 mL). The combined organic layer was dried over Na$_2$SO$_4$, and the solvent was removed under reduced pressure. Crude product was purified by column chromatography (EtOAc/MeOH, 20:1) to give compound 69 (0.234 g, 66%). $^1$H NMR (400 MHz, CDCl$_3$): δ 7.20 (d, J=8.4 Hz, 2H), 7.01 (d, J=2.4 Hz, 1H), 6.82 (d, J=8 Hz, 2H), 6.76 (dd, J$_1$=8 Hz, J$_2$=2.4 Hz, 1H), 6.55 (d, J=8.0 Hz, 1H), 4.81 (bs, —NH$_2$, 2H), 4.71 (s, 2H), 4.62 (t, J$_1$=6.4 Hz, 2H), 4.32 (t, J$_1$=6.8 Hz, 2H), 3.75 (s, 3H), 3.08-3.06 (m, 5H), 2.69-2.44 (m, 14H), 1.99-1.96 (m, 1H), 1.72-1.68 (m, 1H), 1.48-1.43 (m, 2H), 0.87 (t, J=7.2 Hz, 3H); $^{13}$C NMR (100 MHz, CDCl$_3$): δ 173.2, 165.5, 159.0, 148.2, 144.9, 136.6, 128.5, 127.4, 124.6, 119.0, 117.3, 114.2, 114.1, 110.1, 102.6, 65.8, 58.5, 58.0, 55.2, 53.6, 53.5, 49.9, 48.3, 42.9, 26.5, 25.7, 25.0, 22.2, 11.8.

(S)-5-(4-(4-(2-((2-amino-4,5,6,7-tetrahydrobenzo[d]thiazol-6-yl)(propyl)amino)ethyl) piperazin-1-yl)phenyl)indoline-2,3-dione (70)

To a solution of 69 (0.05 g, 0.079 mmol) in 1:1 mixture of Conc. HCl and methanol (6 mL) was taken in a sealed tube. After that, the mixture was heated to 110° C. for 12 h. The reaction mixture was quenched with a saturated solution of NaHCO$_3$ at 0° C. and extracted with dicholoromethane (3×100 mL). The combined organic layer was dried over Na$_2$SO$_4$, and the solvent was removed under reduced pressure. Crude product was purified by column chromatography (CH$_2$Cl$_2$/MeOH, 20:1) to give compound 70 (0.03 g, 69%). The pure amine was dissolved in 20:1 mixture of CH$_2$Cl$_2$:MeOH (0.5 mL), then added 2 M HCl (5 mL) at room temperature and stirred for 10 min. Evaporate the solvent using N$_2$ and then wash with ether followed by vaccume dry to form HCl salt of 70. Free amine: $^1$H NMR (400 MHz, CDCl$_3$): δ 8.56 (s, —NH, 1H), 7.16-7.12 (m, 2H), 6.80 (d, J=8.8 Hz, 1H), 4.99 (bs, —NH$_2$, 2H), 3.13-3.10 (m, 4H), 3.04-3.01 (m, 1H), 2.72-2.44 (m, 14H), 1.99-1.96 (m, 1H), 1.73-1.69 (m, 1H), 1.49-1.43 (m, 2H), 0.88 (t, J=7.2 Hz, 3H); $^{13}$C NMR (100 MHz, CDCl$_3$): δ 183.7, 165.9, 148.5, 144.7, 142.5, 135.4, 126.6, 118.5, 117.1, 113.0, 112.7, 58.5, 58.0, 53.46, 49.6, 48.3, 41.3, 29.6, 26.4, 25.8, 25.0, 22.3, 11.8. LRMS (ESI) m/z [M+H]$^+$: calcd. for C$_{24}$H$_{33}$N$_6$O$_2$S: 469.2386. found: 469.4826. The product was converted into corresponding hydrochloride salt. Mp: 312-314° C.; Anal. (C$_{24}$H$_{32}$N$_6$O$_2$S.4HCl.2H$_2$O).

The following table provides inhibition constants for displacing [3H]spiperone binding to the cloned D$_{2L}$ and D$_3$ receptors expressed in HEK cells. Results are means±SEM for 3 experiments each performed in triplicate. NR=Not repeated.

| Compound | Ki, (nM), D2L [$^3$H]Spiperone | Ki, (nM), D3 [$^3$H]Spiperone |
|---|---|---|
| 22 (D-547) | 2,404 ± 29 | 15.8 ± 2.0 |
| 23 (D-548) | 175 ± 8 | 3.62 (4) ± 0.78 |
| (−)-23 (D-591) | 68.3 ± 12.0 | 1.57 ± 0.41 |
| 34 (D-584) | 116 ± 8 | 2.59 ± 0.31 |
| (−)-34 (D-593) | 65.7 ± 11.7 | 1.42 ± 0.14 |
| 35 (D-584) | 117 ± 17 | 1.01 ± 0.28 |
| (−)-36 (D-601) | 112 ± 8 | 0.78 ± 0.2 |
| 39 (D-567) | 233 ± 8 | 23.3 ± 4.0 |

-continued

| Compound | Ki, (nM), D2L [$^3$H]Spiperone | Ki, (nM), D3 [$^3$H]Spiperone |
|---|---|---|
| 46, 47 (D-592) | 121 ± 21 | 25.0 ± 1.96 |
| 54 (D-573) | 499 ± 16 | 11.9 ± 1.9 |
| 63 (D-570) | 4,634 ± 325 | 39.1 ± 5.4 |
| 70 (D-588) | 162 ± 7 | 14.2 ± 3.8 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula IA or IB for treating neurodegenerative and other related CNS diseases:

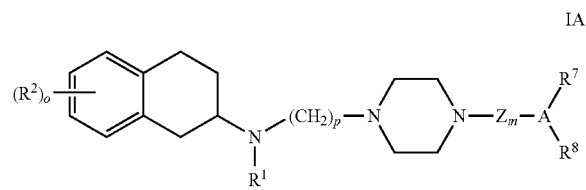

IA

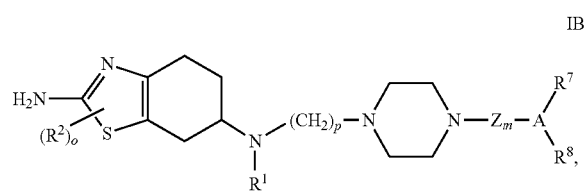

IB or a pharmaceutically acceptable salt or ester thereof, wherein $R^1$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;

$R^2$ are hydroxyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, —$NR^3_q$ or $C_{1-10}$ hydrocarbon groups containing one or more O, N, S, or Se heteroatoms where $R^3$ individually are H or organyl groups and q is 2 or 3, with the proviso that when q is 3, the group bears a positive formal charge;

$R^7$, $R^8$ are each independently, hydrogen (H), hydroxyl, =O, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or —$NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

A is optionally substituted bipyridyl;

p is an integer from 1 to 6;

$Z_m$ is absent; and o is 0, 1, 2, 3, or 4 for formula IA and 0 for formula IB.

2. The compound of claim 1 wherein $R^1$ is substituted with a component selected from the group consisting of $C_{1-8}$ alkoxy, $C_{1-4}$ acyloxy, $C_{1-4}$ acyl, —C(O)—$R^4$, —$R^5$—NH—SO$_2$—$NR^4_r$, —$R^5$—NH—C(O)—$R^4$; —$R^5$—$NR^4_r$, and —$R^5$—Ar where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

$R^5$ is $C_{2-8}$ alkenyl;

r is 2 or 3; and

Ar is a $C_{6-10}$ aryl ring system, optionally including one or more heteroatoms or $C_{5-10}$ heteroaryl;

with the proviso that when r is 3, the nitrogen of the $NR^4_r$ group will bear a positive formal charge.

3. The compound of claim 2 wherein Ar is an optionally substituted phenyl, thienyl, pyridyl, bipyridyl, biphenylyl, or naphthyl.

4. The compound of claim 1 wherein $R^2$ are $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl; $C_{6-10}$ aryl, or —$NR^3_q$, where $R^3$ individually are H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl where q is 2 or 3, with the proviso that when q is 3, the group bears a positive formal charge and wherein hydrocarbon groups in each case are optionally substituted with —CN, $C_{1-8}$ alkyl, —$OR^3$, —OH, halo, or —$CF_3$.

5. The compound of claim 4 wherein two $R^2$ together form an alicyclic or aromatic fused five or six membered ring, optionally containing heteroatoms O, N, S, or Se.

6. The compound of claim 1 wherein A is substituted with $C_{1-8}$ alkyl, —CN, halo, OH, $C_{1-8}$ alkoxyl, $NH_2SO_2R^3$, $CF_3$, arylsulfonyl, arylsulfonamide, o-OCH$_3$, 2,3-dichloro, pyridinyl, bipyridinyl, or p-NHSO$_2$CH$_3$.

7. A compound selected from the group consisting of:

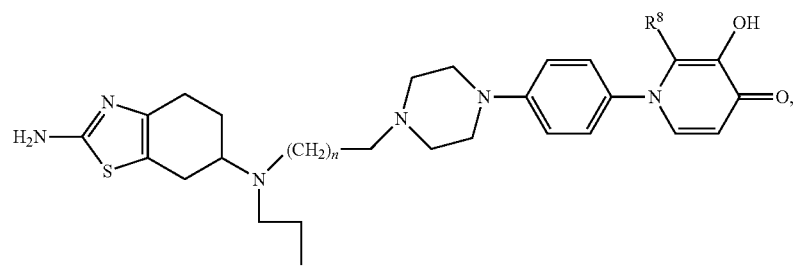

-continued

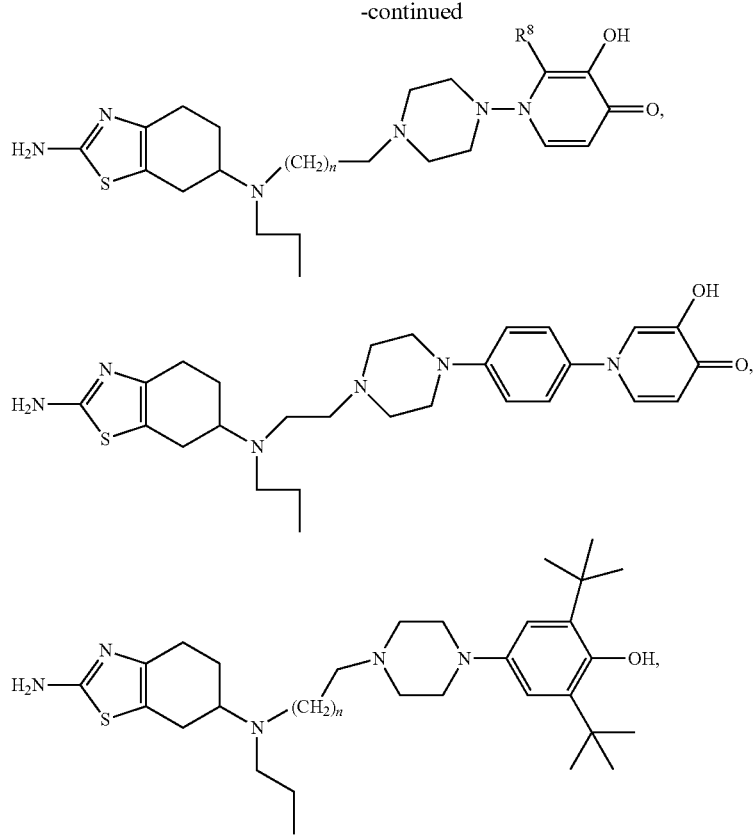

and
pharmaceutically acceptable salts thereof,
wherein:
R$^8$ is hydrogen (H), hydroxyl, =O, C$_{1-8}$ alkyl, C$_{1-8}$ alkoxyl, C$_{2-8}$ alkenyl, C$_{2-10}$ alkynyl, C$_{5-7}$ cycloalkyl, C$_{5-7}$ cycloalkenyl, halo, C$_{1-4}$ aldehyde, or —NR$^4_q$ where R$^4$ is H, C$_{1-8}$ alkyl, C$_{2-8}$ alkenyl, C$_{4-8}$ cycloalkyl, C$_{4-8}$ cycloalkenyl, or C$_{6-10}$ aryl; and
n is 1, 2, 3, 4, 5, or 6.

8. The compound of claim 7 wherein R$^8$ is hydrogen (H), hydroxyl, C$_{1-8}$ alkyl, C$_{1-8}$ alkoxyl, C$_{2-8}$ alkenyl, C$_{2-10}$ alkynyl, C$_{5-7}$ cycloalkyl, C$_{5-7}$ cycloalkenyl, halo, C$_{1-4}$ aldehyde, or —NR$^4_q$ where R$^4$ is H or organyl groups and q is 2 or 3.

9. The compound of claim 8 wherein R$^4$ is H, C$_{1-8}$ alkyl, C$_{2-8}$ alkenyl, C$_{2-10}$ alkynyl, C$_{4-8}$ cycloalkyl, C$_{4-8}$ cycloalkenyl, or C$_{6-10}$ aryl.

10. A compound selected from the group consisting of:

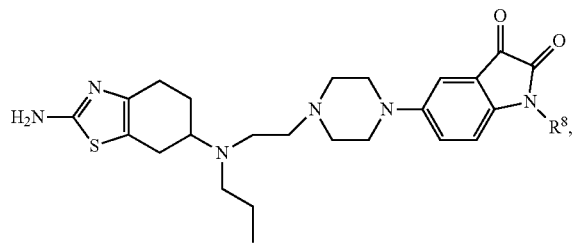

-continued
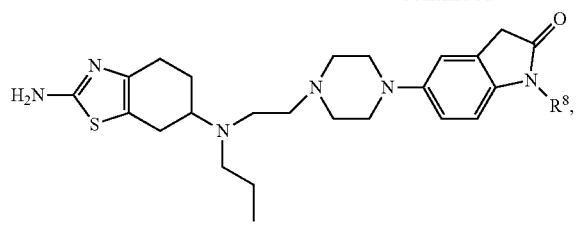
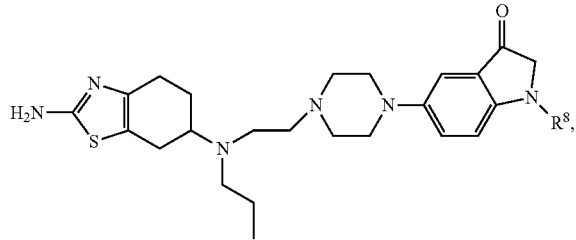
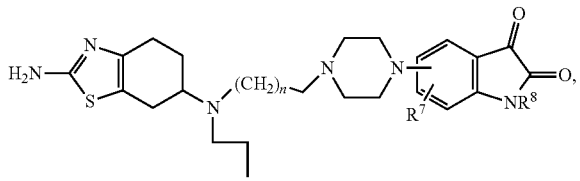
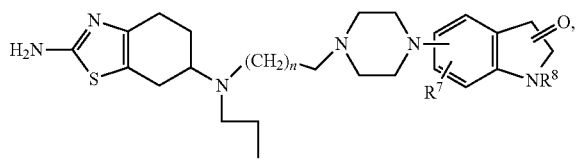
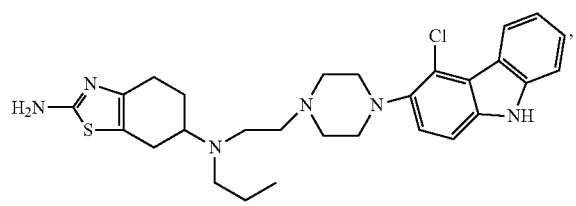
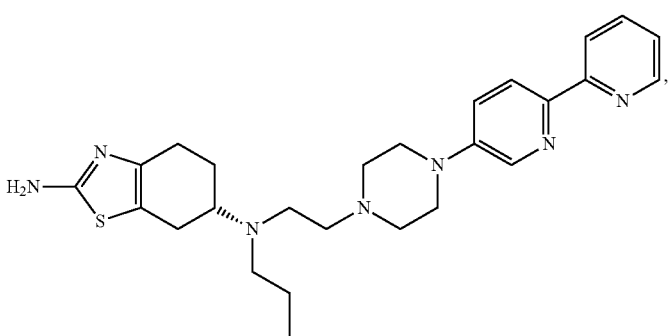
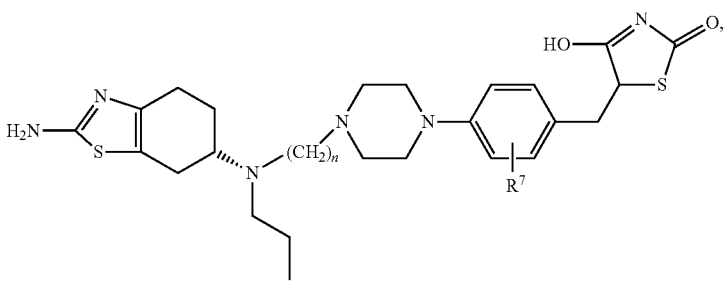

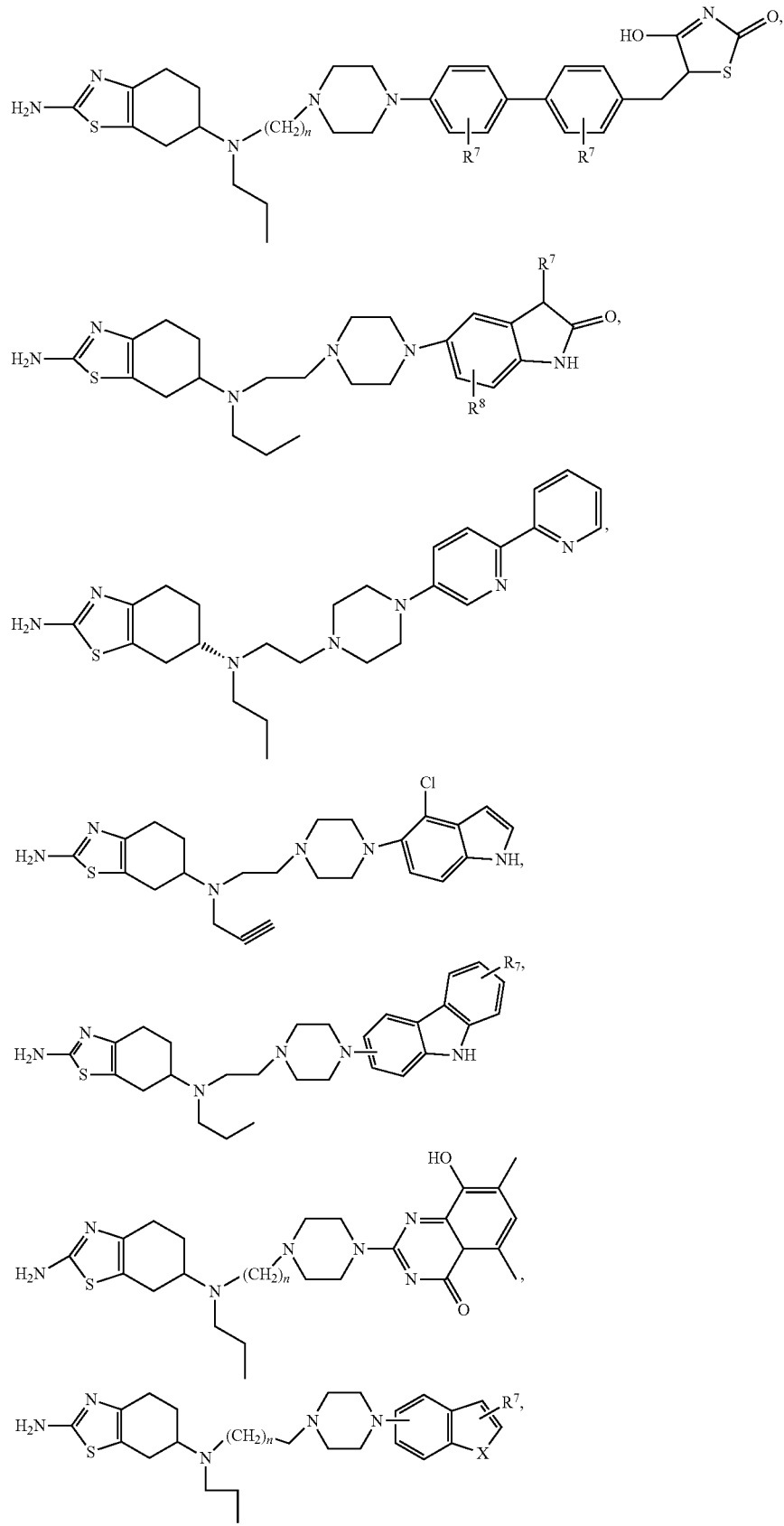

and pharmaceutically acceptable salts thereof, wherein:

X is $NR^2$, O, or S;

$R^2$ is H or $C_{1-10}$ alkyl;

$R^7$, $R^8$ are each independently, hydrogen (H), hydroxyl, =O, $C_{1-8}$ alkyl, $C_{1-8}$ alkoxyl, $C_{2-8}$ alkenyl, $C_{2-10}$ alky-nyl, $C_{5-7}$ cycloalkyl, $C_{5-7}$ cycloalkenyl, halo, $C_{1-4}$ aldehyde, or $-NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

q is 2 or 3; and n is 1, 2, 3, 4, 5, or 6.

11. A compound selected from the group consisting of:

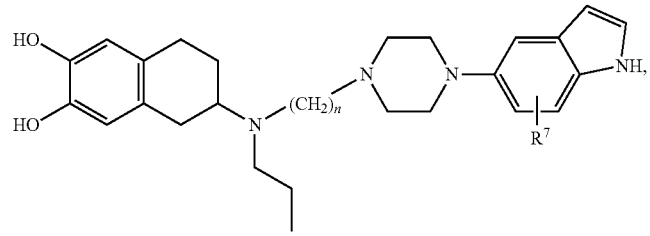

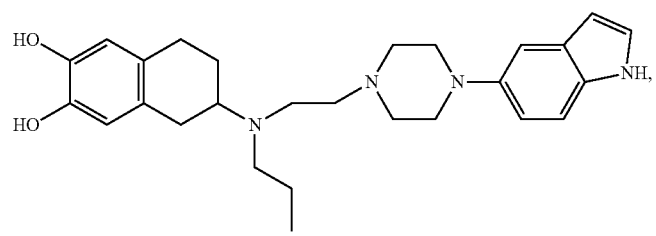

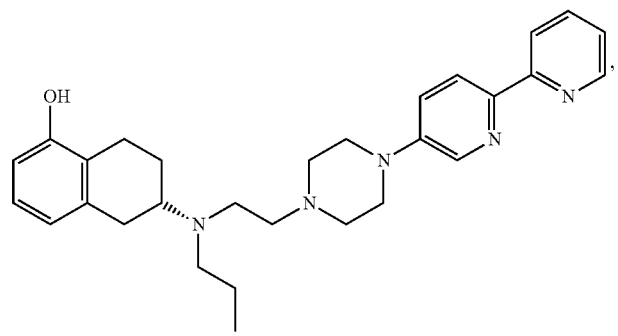

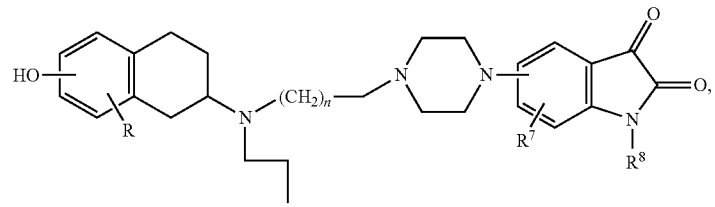

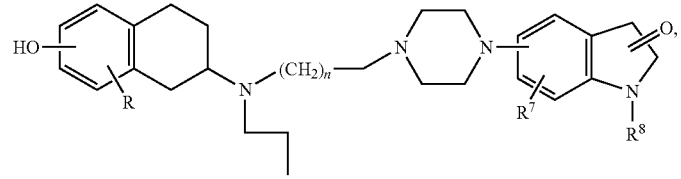

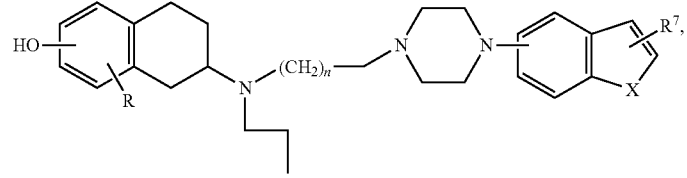

-continued

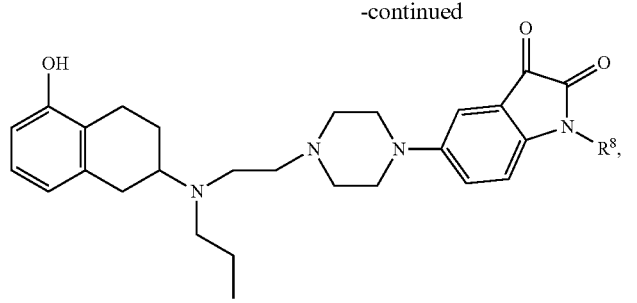

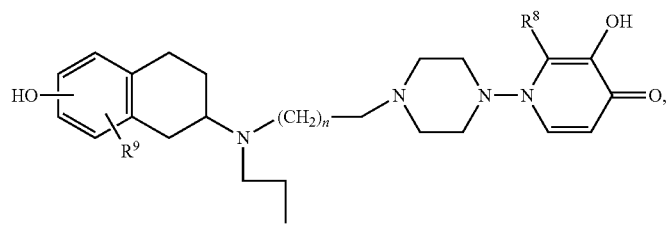

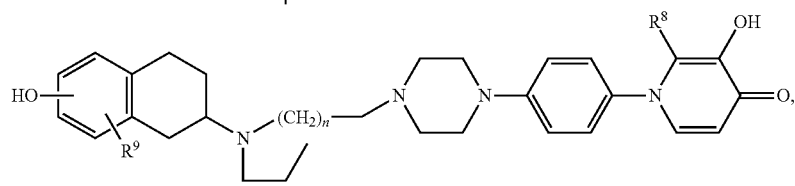

and
pharmaceutically acceptable salts thereof,
wherein:
X is NR², O, or S;
R is H or $C_{1-10}$ alkyl;
R² is H or $C_{1-10}$ alkyl;
R⁷, R⁸ are each independently, hydrogen (H), hydroxyl, =O, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or —NR$^4_q$ where R⁴ is H, $C_{1-8}$ alkyl, $C_{2-8}$ alkenyl, $C_{4-8}$ cycloalkyl, $C_{4-8}$ cycloalkenyl, or $C_{6-10}$ aryl;
q is 2 or 3;
R⁹ is H or $C_{1-10}$ alkyl; and
n is 1, 2, 3, 4, 5, or 6.

12. A compound having formula IA or IB for treating neurodegenerative and other related CNS diseases:

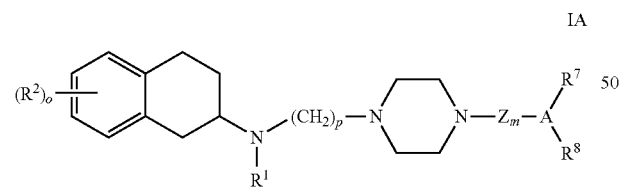

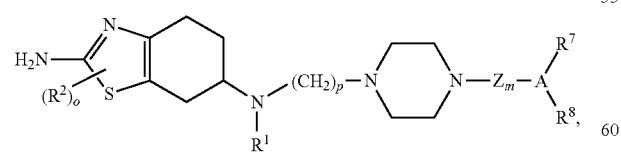

or a pharmaceutically acceptable salt or ester thereof,
wherein
R¹ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;

R² are hydroxyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, —NR$^3_q$ or $C_{1-10}$ hydrocarbon groups containing one or more O, N, S, or Se heteroatoms where R³ individually are H or organyl groups and q is 2 or 3, with the proviso that when q is 3, the group bears a positive formal charge;

A is

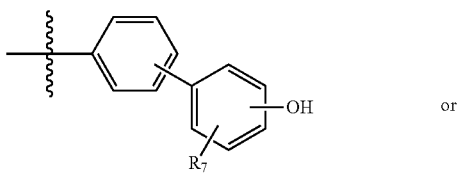

or

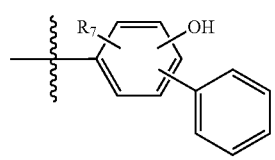

R⁷ is hydroxyl, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or —NR$^4_q$ where R⁴ is H, $C_{1-8}$ alkyl, $C_{2-8}$ alkenyl, $C_{4-8}$ cycloalkyl, $C_{4-8}$ cycloalkenyl, or $C_{6-10}$ aryl;

p is an integer from 1 to 6;

$Z_m$ is absent; and o is 0, 1, 2, 3, or 4 for formula IA and 0 for formula IB.

13. A compound selected from the group consisting of:

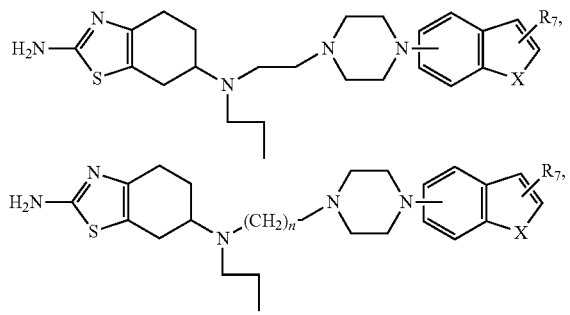

and
pharmaceutically acceptable salts thereof,
wherein:
X is NH, O, or S; and
R$^7$ is hydrogen (H), hydroxyl, =O, C$_{1-8}$ alkyl, C$_{1-8}$ alkoxyl, C$_{2-8}$ alkenyl, C$_{2-10}$ alkynyl, C$_{5-7}$ cycloalkyl, C$_{5-7}$ cycloalkenyl, halo, C$_{1-4}$ aldehyde, or —NR$^4{}_q$ where R$^4$ is H, C$_{1-8}$ alkyl, C$_{2-8}$ alkenyl, C$_{4-8}$ cycloalkyl, C$_{4-8}$ cycloalkenyl, or C$_{6-10}$ aryl;
q is 2 or 3; and
n is 1, 2, 3, 4, 5, or 6.

14. A compound selected from the group consisting of:

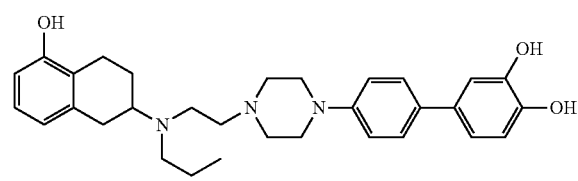

and pharmaceutically acceptable salts thereof.

15. A compound selected from the group consisting of:

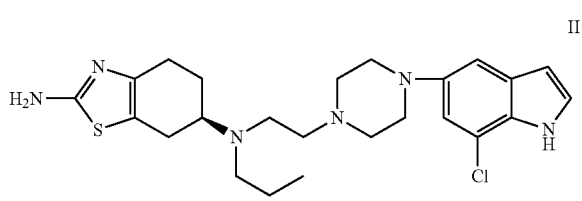 [SMILES: CCCN(CCN1CCN(c2cc(Cl)c3[nH]ccc3c2)CC1)[C@@H]1CCc2nc(N)sc2C1]

and pharmaceutically acceptable salts and esters thereof.

16. A compound selected from the group consisting of:

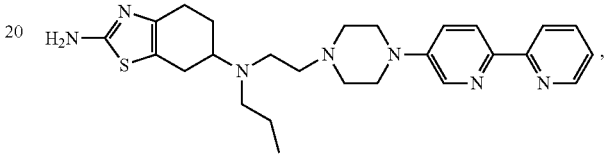

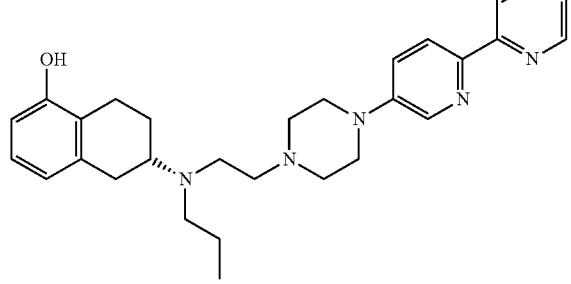

and pharmaceutically acceptable salts and esters thereof.

* * * * *